(12) United States Patent
Bornstein

(10) Patent No.: US 8,430,919 B2
(45) Date of Patent: Apr. 30, 2013

(54) OPTICAL METHOD AND DEVICE FOR MODULATION OF BIOCHEMICAL PROCESSES IN ADIPOSE TISSUE

(75) Inventor: Eric Bornstein, Brooklyn, NY (US)

(73) Assignee: Nomir Medical Technologies, Inc., Natick, MA (US)

( * ) Notice: Subject to any disclaimer, the term of this patent is extended or adjusted under 35 U.S.C. 154(b) by 0 days.

(21) Appl. No.: 13/182,284

(22) Filed: Jul. 13, 2011

(65) Prior Publication Data
US 2012/0116484 A1     May 10, 2012

Related U.S. Application Data

(63) Continuation of application No. 11/657,809, filed on Jan. 24, 2007, now abandoned.

(60) Provisional application No. 60/761,717, filed on Jan. 24, 2006, provisional application No. 60/781,260, filed on Mar. 9, 2006.

(51) Int. Cl.
*A61N 5/06*     (2006.01)

(52) U.S. Cl.
USPC .............................. 607/88; 606/9

(58) Field of Classification Search .................. None
See application file for complete search history.

(56) References Cited

U.S. PATENT DOCUMENTS

| | | | | |
|---|---|---|---|---|
| 6,443,978 | B1 * | 9/2002 | Zharov | 607/91 |
| 7,081,128 | B2 * | 7/2006 | Hart et al. | 607/89 |
| 7,959,656 | B2 * | 6/2011 | Myeong et al. | 607/88 |
| 2004/0093042 | A1 * | 5/2004 | Altshuler et al. | 607/88 |
| 2004/0181210 | A1 * | 9/2004 | Shellman | 606/8 |
| 2008/0208296 | A1 * | 8/2008 | Smith et al. | 607/89 |

OTHER PUBLICATIONS

Examination Report for European Application No. 07762552.3 dated Aug. 23, 2012.
US Office Action on U.S. Appl. No. 11/657,809 DTD Jan. 14, 2011.

* cited by examiner

*Primary Examiner* — Bill Thomson
*Assistant Examiner* — Lynsey Crandall
(74) *Attorney, Agent, or Firm* — Foley & Lardner LLP; Matthew L. Fenselau

(57) ABSTRACT

Optical methods and devices are provided for the reduction of the lipid content of adipocytes without significant heat or intolerable adverse effect on the cells and their surrounding tissues. The optical method and device can be used to irradiate adipose tissue through the skin with non-thermal and non-destructive effects by application of near infrared (NIR) irradiation at selected wave bands in selected ranges to affect modulation of innate enzymatic processes involved in lipolysis, lipogenesis, leptin secretion, adiponectin secretion, and/or glucose absorption.

22 Claims, 15 Drawing Sheets

Multiple LED arrays, all with separate collimating lenses in Dispersion Belt

Absorption spectrum of water.

OPTICAL METHOD AND DEVICE FOR MODULATION OF BIOCHEMICAL PROCESSES IN ADIPOSE TISSUE

RELATED APPLICATIONS

This patent application is a continuation of U.S. patent application Ser. No. 11/657,809, filed Jan. 24, 2007, which claims priority to U.S. provisional application Ser. No. 60/761,717, filed on Jan. 24, 2006, and U.S. provisional application Ser. No. 60/781,260, filed on Mar. 9, 2006, the contents of which are expressly incorporated herein by reference.

FIELD OF THE DISCLOSURE

This disclosure relates to an optical method and device for generating infrared optical radiation in selected wavebands over large skin areas, to modulate adipocyte's lipolytic and lipogenic energy metabolism in subcutaneous tissues. The method and device of the disclosure can be used (alone) during exercise, or in combination with pharmacological means to biochemically alter triglyceride levels in adipocytes.

BACKGROUND

Obesity is a disorder of multiple etiologies, with an onset and development in human beings that has been recognized as having genetic, environmental, and behavioral factors. Obesity is a significant health problem in the developed world and is becoming an increasingly larger problem in the developing world. For example, in the American adult population, one out of three people is considered obese. Obesity is defined by the United States Centers for Disease Control and Prevention (CDC) as an excessively high amount of body fat or adipose tissue in relation to lean body mass and overweight as an increased body weight in relation to height, when compared to some standard of acceptable or desirable weight. The CDC alternatively defines overweight as a person with a body mass index (BMI) between 25.0 and 29.9 and obesity is defined as a BMI greater than or equal to 30.0. Obese and overweight mammals suffer from increased joint problems, increased rates of high blood pressure, and high cholesterol. Increased weight is also associated with heart disease, stroke and diabetes. In 1998, for example, consumers spent $33 billion in the United States for weight-loss products and services with very little success (Serdula, et al., Prevalence of Attempting Weight Loss and Strategies for Controlling Weight, JAMA 282:1353 1358, 1999). Thus, obesity and its associated complications continue to be a major problem throughout the worldwide health care system.

Excessive adipose tissue in the human body, resulting from either genetic or environmental factors, will cause a variety of additional symptoms associated with chronic disease states. These disease states include, but are not limited to, hyperlipidaemia, coronary atherosclerosis, severe carbohydrate intolerance, gout, gall bladder disease, degenerative arthritis, cancer, and infertility.

Currently there are no real cures or non-invasive treatments for obesity. Of the currently known techniques for treating obesity, the most prevalent are pharmacological attempts to suppress appetite or to inhibit intestinal absorption of nutrients. Pharmacological solutions to the problem of obesity generally take one of three different approaches:

1) Pharmacological approach to affect the brain;
2) Pharmacological approach to affect lipid absorption during meals; and
3) Pharmacological approach to affect fat cells per se.

A significant drawback to these approaches is that with the use of any drug to affect these mechanisms, there are a myriad of potential side effects, such as potential central nerves system (CNS) problems and problems with absorption of critical fat and fat-soluble soluble nutrients, that contribute to the early termination of such therapies. Available pharmacotherapies have included Sibutramine, Orlistat™, fenfluramine and dexfenfluramine. Fenfluramine and dexfenfluramine were withdrawn from the market in 1997 because of associated cardiac valvulopathy (Connolly, et al., Valvular Heart Disease Associated With Fenfluramine-Phentermine, New Engl J Med 337 581 588, 1997). Consequently, many health care professionals are reluctant to use pharmacotherapy in the management of obesity. Complimentary approaches to pharmacotherapy may therefore be of great interest to the public.

There are other moderately effective approaches for weight loss or treating obesity, such as behavioral modification, diets, and surgery. To date, the results of all of these approaches have been unsatisfactory, and usually only a moderate proportion of adipose reduction is achieved, but rarely maintained. Although behavioral modification and dietary restriction might be the most desirable methods for weight loss, long-term success of dietary regulation is low because of noncompliance. The loss of motivation to change behavioral and dietary habits necessary to consume less fat and fewer calories results in regaining weight.

Of surgical methods available, suction lipectomy, commonly known as liposuction, is the most common procedure for removing subcutaneous fat in the body. In general, the procedure involves the use of a special type of curette or cannula which is coupled to an external source of suction. An incision is made in the target area and the fatty tissue is essentially vacuumed from the patient's body. This procedure has its disadvantages, however, because the fat is relatively difficult to separate from the surrounding tissue. Such separation often causes excessive bleeding and damage to adjacent tissue or muscles. Other than causing collateral damage to surrounding muscle, blood vessels, skin, nerve, and subcutaneous tissues, liposuction can result in unattractive loose skin, postoperative hemorrhagic complications, pain, trauma, infection, and even death.

In addition to physical injuries associated with liposucion, it has been experimentally and clinically shown that the removal of large amounts of abdominal subcutaneous fat via liposuction does not appreciably alter the levels of circulating mediators of inflammation, that are almost certainly involved in the development of insulin resistance, Diabetes and coronary heart disease.

Adipose tissue is now documented as a significant endocrine organ that produces numerous bioactive proteins, including interleukin-6, tumor necrosis factor (alpha), and adiponectin. The production of adiponectin by adipose tissue can improve insulin sensitivity and inhibit vascular inflammation, while interleukin-6 and tumor necrosis factor (alpha) are known to cause insulin resistance, diabetes, atherosclerosis by damaging insulin signaling, increasing hepatic synthesis of C-reactive protein, and increasing systemic inflammation. As stated above, since it has been experimentally and clinically shown that the removal of large amounts of abdominal subcutaneous fat via liposuction does not appreciably alter the levels of circulating mediators of inflammation (markers of insulin resistance, diabetes and coronary heart diseas) there is a need in medical therapy to achieve a device and therapy that can augment naturally occurring lipolytic activity.

Weight-loss that is achieved by conventional obesity treatments (diet and exercise) decreases plasma concentrations of C-reactive protein, interleukin-6, and tumor necrosis factor-alpha and increases the concentration of adiponectin. In stark contrast, liposuction does not significantly change the plasma concentrations of any of these markers. Additionally, fat removal by liposuction has been shown to decrease plasma leptin concentration, which is a marker of adipose-tissue mass, which is not desirable as it has been implicated as a potent appetite suppressant.

Despite its undesirable side-effects, liposuction is still being used extensively. Various new methods have been devised to augment the procedure by taking advantage of the ultrasonic vibrations or laser energy to physically melt the fatty tissue so that it can be emulsified and aspirated through the liposuction probe. These ultrasonic probes have reduced the physical exertion required by the surgeon to remove fatty tissue, increased the speed of the operation and reduced collateral damage created at the incision point. One problem with these probes, however, is excess heat generation at the distal tip of the probe, which can readily be in excess of the temperature required for melting the fatty tissue. This excess heat often results in burning of tissue, damaging muscles or blood vessels, and even penetrating membranes such as the skin or the peritoneum that covers most of the intra-abdominal organs.

Among the methods that exploit laser energy to remove unwanted fat, U.S. Pat. Nos. 6,605,080 and 7,060,061 issued to Altshuler, et al. represent an alternative approach in which laser energy is externally applied to the skin to heat and melt fat tissues in epidermis and subcutaneous layers below. These patents disclose the use of near infrared radiation to heat-liquefy fat cells, after which the lipid pool is removed from the subcutaneous area by aspiration. Because of the considerable heat generation that results from the techniques, e.g., up to 70° C., at or in the fat tissue, a special cooling mechanism must be in place to prevent potential temporary skin damage or permanent scarring, with permanent scarring occurring primarily in the dermis. These methods present other limitations and potential adverse thermal effects on tissue above the lipid-rich tissue under treatment, including blistering, peeling, and depigmentation.

Therefore, there remains a need for an improved non-invasive method and device for reducing fat and alleviating obesity without excessive heat deposition at the site of treatment; a technique which does not suffer from the noted limitations of the background art; and a method and device that can be utilized by the general public with convenience and ease.

SUMMARY

The present disclosure addresses the limitations noted for the background art and provides a method and device for reducing the level of fat or lipid in adipocytes without significant generation of heat or an intolerable adverse effect to the skin or surrounding tissue. In general, a target site on an individual is irradiated with a near infrared radiation in a first wavelength band or range from about 905 nm to about 945 nm and/or a second wavelength band or range from about 850 nm to about 879 nm at a suitable power dosimetry, e.g., from about 0.015 W/cm$^2$ to 1 W/cm$^2$, to modulate (e.g., potentiate or increase) innate, and already occurring, biochemical processes of adipocytes in the target site. Preferably, the wavelength band of the optical radiation ranges from about 925 nm to about 935 nm. Each of the wavelength bands may be used to irradiate the target site alone or in combination with the other band, sequentially or simultaneously in tandem. The optical radiation can be collimated, for example in applications where an incoherent light source is used to generate the desired wavelengths bands.

In exemplary embodiments, the optical radiation can be provided to the target site for a time period of about 10 to about 120 minutes; preferably, for a period of about 15 to about 100 minutes; or more preferably, for a period of about 20 to 80 minutes. Other applications times may also be used.

As described herein, the techniques, methods, devices, and systems of the present disclosure, may be referred to as Low Dosimetry Optical Adipocte Modulation (LDOAM); certain features of the embodiments may also be referred to as Near Infrared Microbial Elimination Laser Systems (NIMELS). In accordance with exemplary embodiments of the disclosure, the LDOAM dosimetry can provide an energy density from about 10 J/cm$^2$ to about 10,000 J/cm$^2$ at the skin surface above the adipose tissue; alternatively, the provided energy density is from about 50 J/cm$^2$ to about 8,000 J/cm$^2$ at the skin surface above the adipose tissue; or alternatively, the energy density is from about 100 J/cm$^2$ to about 5,000 J/cm$^2$ at the skin surface above the adipose tissue.

According to aspects of the disclosure, the biochemical processes modulated by the LDOAM optical dosimetry can include, but are not limited to, lipolysis and lipogenesis. Preferably, these processes already are in progress when LDOAM is used, e.g., as would be the case when a person is participating in sport and exercise activities or when such processes are initiated or facilitated by pharmacological means, with or without exercise.

In exemplary embodiments of the disclosure, LDOAM radiation is generated by Light Emitting Diode (LED) arrays or by arrays of super-luminous LEDs. Preferably, LEDs are arrayed with aspheric collimating lenses within a body wrap. Alternatively, or in addition, suitable laser diodes may be used.

Other aspects of the present disclosure provide a device including one or more suitable optical light sources, such as LED arrays, for generating LDOAM radiation. In exemplary embodiments of this aspect of the invention, LED arrays with one or more aspheric collimating lenses are configured and arranged within an article of clothing. Such article of clothing can include means for attaching to a power source (e.g., a suitable power connection) and can be worn by a person while using sports or exercise equipment (i.e., treadmill, bike, or weights) to facilitate fat reduction. The power source can operate by battery or electricity.

Additional functionality, advantages, and embodiments of the disclosure are described in the following description and included drawings.

It is to be understood that both the foregoing general description and the following detailed description are exemplary and explanatory only and are not restrictive of the disclosure, as claimed.

BRIEF DESCRIPTION OF THE DRAWINGS

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. Where applicable, the same reference numbers are used throughout the drawings to refer to the same or like parts or features. In the drawings.

DETAILED DESCRIPTION

Figure 1:
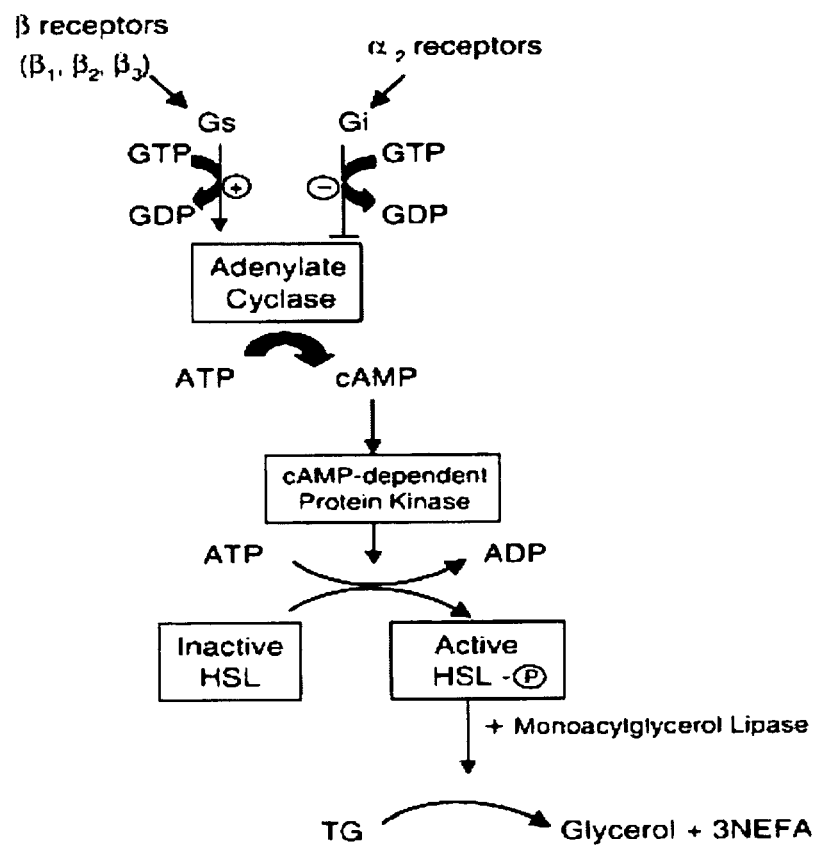
FIG. 1 is a flow chart diagram depicting enzymatic steps involved in the biochemical process of lipolysis in a human adipocyte.

Reference will now be made in detail to exemplary embodiments of the present disclosure, an example(s) of which is (are) illustrated in the accompanying drawings. As noted previously, the same reference numbers are used throughout the drawings, where applicable, to refer to the same or like parts or features.

The present disclosure relates generally to a method and device for irradiating adipose tissue that is already undergoing biochemical lipolysis, and more specifically adipocyte cell membranes, with non-thermal and non-destructive effects by application of near infrared (NIR) radiation at desired wavelengths to effect modulation of already occurring enzymatic processes within the adipocyte, e.g., during exercise or digestion. According to certain embodiments of the disclosure, these processes may already be in progress, e.g., by sport and exercise activities, digestion, or by pharmacological means, when optical radiation is applied. Certain aspects of the disclosure provide a method and/or device for the selective modulation of adipocyte metabolism in subcutaneous fat by using light in specific NIR bands or spectral ranges to effect biochemical modulation of adipocytes over large cutaneous area during exercise or digestion without detrimental photothermal effects, photothermal alteration and/or photothermal destruction of any part of the adipocyte, adipocyte cell membrane or adipose tissues. As described in further detail herein, suitable light sources can include, for example, light emitting diodes (LEDs) or super-luminous light emitting diodes (LEDs), or other suitable light sources generating radiation in selected wavelength bands. As described herein, such techniques, methods, and systems, may be referred to as Low Dosimetry Optical Adipocte Modulation (LDOAM); certain features of the embodiments may also be referred to as Near Infrared Microbial Elimination Laser Systems (NIMELS).

Generally stated, aspects of the present disclosure can provide a method and system useful for irradiating adipose tissue to effect modulation of already occurring biochemical processes within the adipocyte. As desired, the method/system irradiates adipose tissue (to augment or suppress biochemical processes such as Lipolysis) with energy from light emitting diodes (LEDs) or other suitable light sources, at the effective wavelength bands or ranges (preferentially absorbed by chromophores in the adipocytes) in the near infrared (NIR) range. Preferably, the NIR ranges are those such that the ratio of the scattering coefficient of the photons on human skin ($\mu s$) to the absorption coefficient in human skin ($\mu a$) or ($\mu s/\mu a$), is at least a value of about 40. Such near infrared radiation may be in wavelength bands between about 850 nm and about 879 nm and about 900 nm and about 940 nm, and may be delivered with a Power Density ($W/cm^2$), temporal characteristics, and/or energy density (fluence or $J/cm^2$) sufficient to modulate desired pre-initiated adipocyte biochemical processes.

In one embodiment, this may occur in the absence of any substantial heat rise of greater than about 5 degrees Celsius. Also, as desired, the method/system will irradiate adipose tissue (to augment or suppress biochemical processes such as Lipogenesis, Leptin secretion, and glucose absorption) with energy from Light Emitting Diodes or other suitable light source, at the given wavelength bands stated above. The methods and system of this disclosure may be used to modulate (up-regulate or down-regulate) one or more of the biochemical processes of Lipolysis, Lipogenesis, Leptin Secretion, and Glucose absorption in the adipocyte which could lead to the reversal of negative physiological effects such as obesity and c-reactive protein.

Further summarizing the disclosure, various embodiments may be implemented for a method and system for irradiating adipose tissue to effect modulation of biochemical processes within the adipocyte.

DEFINITIONS OF TERMS USED

Throughout the specification and claims, including the detailed description below, the following definitions apply.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Other than in the operating examples, or where otherwise indicated, all numbers expressing quantities used in the specification and claims are to be understood as being modified in all instances by the term "about." Accordingly, unless indicated to the contrary, the numerical parameters set forth in the present specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The term "absorbance" as used herein refers to an index of the light absorbed by a medium compared to the light transmitted through it. Numerically, it may be represented by the logarithm of the ratio of incident spectral irradiance to the transmitted spectral irradiance.

The term "dosimetry" as used herein refers to a common, but loosely used, term for energy and/or power density at or across a particular surface or area. The term can be applied to energy and/or power absorbed within the medium of interest. Shortened terms for energy density may be expressed in Joules or milli-Joules per square centimeter, i.e., $J/cm^2$ or $mJ/cm^2$. Shortened terms for power density may be expressed in Watts or milli-Watts per square centimeter, i.e., $W/cm^2$ or $mW/cm^2$.

The term "energy density" or "fluence" as used herein refers to radiant energy arriving at a surface per unit area, usually expressed in joules or milli-Joules per square centimeter ($J/cm^2$ or $mJ/cm^2$). It is the time-integral of irradiance. Terms applied in similar technologies include "radiant exposure," "light dose," and "total effective dosage".

The term "temporal characteristics" as used herein refers to time characteristics of the NIR energy used, and can refer to any one or more of the following terms: pulse width (e.g., in terms of FWHM or 1/e power) of individual pulses, pulse repetition frequency, duty cycle for pulsed applications, and time of application of pulsed or continuous wave (CW) energy.

The term "effective dosimetry" as used herein denotes optical radiation treatments with near infrared radiation, according to the disclosure, at power density and energy density (fluence) effective to achieve the result sought. Furthermore, one of skill will appreciate that the effective amount of the dosimetry of the invention may be lowered or increased by fine tuning and/or by applying more than one suitable light source or by using the LDOAM radiation of the disclosure with another method of reducing fat known in the art. Further, the angular divergence (e.g., in orthogonal directions to a propagation axis) of the light used may be selected or modified as desired, for example by use of one or more collimating lenses. Although other light sources or lasers may have been known and used in removal or reduction of fat, the field has generally remained silent towards the use of a suitable light source at selected wavelengths to initiate, modulate and/or inhibit the innate and occurring enzymatic processes of adipocytes.

The term "article of clothing" or "item of clothing" as used herein refers to any type of clothing such as, but not limited to, a belt, a wrap, a bandage, pants, shorts, belt, wrap, arm band, leg band, a shirt, underwear, outerwear, and any item of clothing and apparel that can be used to implement the general idea of the present disclosure.

The term "light skin" as used herein denotes a person who has a skin type between 1 to 4 on a Fitzpatrick scale for skin type.

The term "fat lowering drug" as used herein refers to any natural or synthetic composition that helps clearing fatty acid and cholesterol from the serum.

The term "moderate aerobic exercise" as used herein refers to any type of activity that increase the hart rate by 20% or more.

The term "immediately following" as used herein denotes the time within ½ hour; preferably, within 0-20 minutes; or more preferably, within 5-15 minutes.

Conditions that can Affect the Rate of Innate Enzymatic Reactions in Adipocytes

In general, the conditions that can potentially affect the rate of enzymatic reactions in Adipocytes are:
1) Substrate concentration changes
2) Enzyme concentration changes
3) Temperature changes
4) Hormonal changes.

Substrate Concentration

At lower concentrations, the active sites on most enzyme molecules are less than optimally filled because there is not much substrate within proximity of the enzyme. Higher concentrations of substrate will cause more collisions between the substrate and enzyme molecules. With more molecules and collisions, enzymes are statistically more likely to come upon molecules of reactant (substrate). Within adipocyte cells, the substrate for the enzymatic reaction of lipolysis makes up about 97% of the volume of the cell. The maximum velocity of a reaction is reached when the active sites of specific enzymes are almost continuously filled with substrate. Therefore, other ways may preferably be used modulate the enzymatic rate of necessary and beneficial reactions like lipolysis, by adding specific wavelengths of (free) energy to the cell membrane of the adipocyte, where many of the important rate-limiting enzymes for lipolysis lay.

Temperature

A higher temperature will generally cause increased collisions among molecules and therefore, increases the rate of an enzymatic reaction. This is normally true because more collisions increase the likelihood that substrate will collide with the active site of the enzyme, thus increasing the rate of an enzyme-catalyzed reaction. However, in the biological system of adipocyte, increased temperature (by even 3 or 4 degrees Centigrade) actually inhibits the reaction rate of lipolysis.

Although other light sources and lasers for the heat-destruction, photo-thermolysis, and/or poration of subcutaneous fat are available, the light sources and lasers used with such procedures have generally functioned at conditions that cannot irradiate areas of tissue greater than a couple of $cm^2$, and cannot be used or operated independent of a trained physician or technician while an individual is exercising. The extreme heat generated by these previous methods usually results in degeneration and destruction of any protein and enzymes within adipocytes and often causes injuries to skin or dermis (with large amount of water and collagen absorbing the radiation energy) above the adipose tissues.

The present disclosure provides a method and device to gently modulate the enzymatic rate of necessary and beneficial reactions like lipolysis, by adding specific wavelength and dosimetry free energy to the adipocyte membrane where many of the important rate-limiting enzymes for liplysis lay, without significantly increasing the muscle, fat, or core temperature of the individual. This is accomplished, in accordance with the disclosure, with Low Dosimetry Optical Adipocte Modulation (LDOAM) techniques implemented in suitable methods and devices as described herein.

In accordance with embodiments of the present disclosure, LDOAM method and devices are used to irradiate adipose tissue (to augment or suppress already occurring biochemical and enzymatic processes such as lipolysis and lypogenesis, respectively) with energy from light emitting diodes or other suitable light sources, at the effective wavelength bands (preferentially absorbed by chromophores in the adipocyte cell membranes and adipocyte mitochondrial membranes) in the near infrared range, where the ratio of the scattering coefficient of the infrared photons on human skin (μs) to the absorption coefficient in human skin (μa) or (μs/μa), is at least a value of 40. In exemplary embodiments, such near infrared wavelengths are in bands between about 850 nm to about 879 nm and about 900 nm to about 940 nm; discrete wavelengths may also be utilized, e.g., at 870 nm and 930 nm. Such energy can be delivered with a Power Density (W/cm$^2$), temporal characteristics, and Energy Density (J/cm$^2$) sufficient to modulate desired—innate and already occurring—adipocyte biochemical enzymatic processes. This occurs in the absence of any substantial heat rise of greater than about 5° C.

In accordance with exemplary embodiments of the disclosure, the LDOAM dosimetry provides an energy density from about 10 J/cm$^2$ to about 10,000 J/cm$^2$ and a power density from about 0.015 W/cm$^2$ to 1 W/cm$^2$. In accordance with yet another embodiment of the disclosure, the provided energy density is from about 50 J/cm$^2$ to about 8,000 J/cm$^2$; or alternatively, it is from about 100 J/cm$^2$ to about 5,000 J/cm$^2$. Other suitable energy densities may be used.

In accordance with one embodiment of the disclosure, the optical radiation is applied for about 10 to about 120 minutes; preferably, for about 15 to about 100 minutes; still more preferably, for about 20 to 80 minutes. Other application times may also be used within the scope of the present disclosure.

The LDOAM methods and devices of the invention can be used to irradiate adipose tissue to augment or suppress biochemical processes such as lipolysis, lipogenesis, leptin secretion, and/or glucose absorption with energy from one or more light emitting diodes or other suitable light source, e.g., suitable laser diodes, at the wavelength bands stated above. Suitable lights sources and methods of generating suitable NIR light can include so-called optical parametric devices, e.g., optical parametric oscillators (OPOs), optical parametric generators (OPGs), optical parametric amplifiers (OPAs), utilizing suitable nonlinear materials to produce (e.g., through frequency shifting) desired NIR light for the LDOAM techniques described herein. The methods and devices of the present disclosure contemplate modulating (up-regulating or down-regulating) one or more of the already occurring biochemical processes of lipolysis, lipogenesis, leptin secretion, and/or glucose absorption in adipocytes.

Lipolysis

Lipolysis is the biochemical breakdown and release of stored fat from adipose tissue. This process normally prevails over lipogenesis when additional energy is a requirement for the person's activities. Triacylglycerol (fat) within the adipocyte is acted upon by a multi-enzyme complex called hormone sensitive lipase (HSL), which hydrolyzes the Triacylglycerol into non-esterified fatty acids (NEFA) and glycerol. The regulation of HSL activity is an important factor in the regulation of biochemical lipolysis and hence the (distal) mobilization of lipids from adipocytes.

Once triglycerides are hydrolyzed to fatty acids and glycerol, fatty acids enter the common free fatty acid pool where they may be re-esterified, undergo beta-oxidation (metabolic degradation), or be released into the circulation as substrates for skeletal muscle, cardiac muscle, and liver. If the fatty acids are to undergo beta-oxidation for ATP production, fatty acids move from the adipocytes into the blood stream and are carried to the tissues that can use them as an energy source.

NEFAs are a significant source of energy (fuel) for metabolic oxidation by working muscle tissue, and the process is normally regulated via hormones during periods of excess energy expenditure, such as exercise.

Generally, entities that participate in a series of intricate enzymatic steps that modulate lipolysis, as shown in FIG. 1, are adrenergic hormonal binding receptors; adenylate cyclase (AC); stimulatory guanine nucleotide binding protein (Gs); inhibitory guanine nucleotide binding protein (Gi); cyclic adenosine monophosphate (cAMP); cAMP—dependent protein kinase; hormone sensitive lipase (HSL); monoacylglycerol lipase; triacylglycerol (TG); glycerol; and non-esterified fatty acids (NEFA). One embodiment of the present disclosure contemplates augmenting lipolysis by affecting any of the entities participating in the lipolysis pathway. The methods of the present disclosure may also affect systemic and local controls of enzymatic modulation over biochemical hydrolysis (lipolysis) or synthesis (lipogenesis) of triacylglycerol.

Lipogenesis

Figure 2:
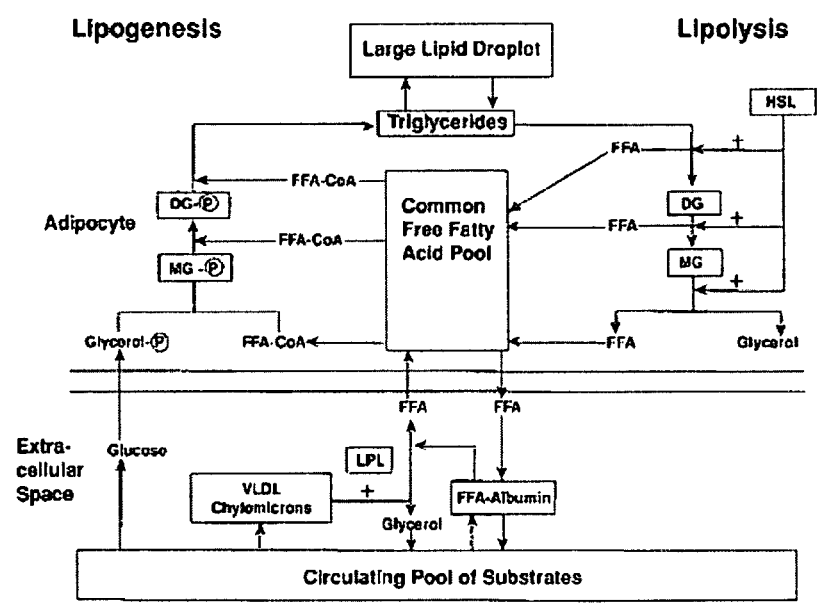
FIG. 2 is a flow chart diagram illustrating enzymatic steps of the biochemical processes of lipogenesis and lipolysis occurring in human adipocytes.

Lipogenesis is a collective name for the complex process of producing triglycerides or fat from smaller precursor molecules such as glucose and free fatty acids. As shown in FIG. 2, lipogenesis and lipolysis both occur in human adipocytes. Modulation of lipogenesis—inhibiting fatty acid synthesis in the adipocyte—may be affected by selectively inhibiting glucose uptake in the adipocyte during this period of time, independent of a drug added to the system. In one embodiment of the disclosure, the regulation of glucose absorption by adipocytes over a large subcutaneous area, i.e., midriff, thighs, buttocks and arms can be modulated with near infrared wavelengths bands, one being between about 850 nm to about 879 nm and/or the other being about 900 nm to about 940 nm, delivered with a Power Density (W/cm$^2$), temporal characteristics, and Energy Density (J/cm$^2$) sufficient to hamper the adipocyte biochemical processes involved in lipogenesis. This can be accomplished over large subcutaneous areas with Low Dosimetry Optical Adipose Modulation (LDOAM) techniques as described herein. The disclosure further contemplates either systemic or local suppression of lipogenesis by modulating any of the related enzymes, as shown in FIG. 2, involved in that pathway.

Leptin

Leptin is widely reported to have a role in the biochemical regulation of rodent appetite and energy expenditure. The hormone Leptin is released by fat cells, as the cells increase in size (lipogenesis) as a direct result of calorie intake. It is also known that circulating Leptin (an appetite suppressor) signals the hypothalamic areas involved with appetite and metabolic rate. It has also been widely reported that circulating levels of Leptin are closely and positively correlated with body fat in humans. In fact, current evidence suggests that multiple factors including Leptin levels both in the brain and periphery may be involved in weight loss and metabolism. The LDOAM method and device of the present disclosure modulate Leptin biochemistry of adipocytes to facilitate fat reduction. According to an embodiment of the disclosure, near infrared wavelengths in bands between about 850 nm to about 879 nm and/or about 900 nm to about 940 nm, with sufficient Power Density (W/cm$^2$), temporal characteristics, and Energy Density (fluence or J/cm$^2$) increase the amount of Leptin normally produced by the adipocytes for potential use in weight loss and fat regulation.

It has been known that exercise decreases plasma leptin without affecting the gene expression level in adipose tissue in humans. Also, others have shown that in humans, isoproterenol (initiated lipolysis) acutely suppresses leptin levels independently of increased FFAs, and elevated FFAs have no acute effect on leptin levels. However, according to in vitro experimentation results with the current disclosure, near infrared wavelengths in bands between about 900 nm to about 940 nm, with sufficient Power Density (W/cm$^2$), temporal characteristics, and Energy Density (fluence or J/cm$^2$) actually re-coupled the leptin release process to isoproterenol induced lipolysis, and increased the amount of Leptin normally produced by the adipocytes during lipolysis. It has also been known that leptin induces a secondary form of lipolysis in adipocytes.

Mechanistically, without wishing to be bound by any theory and not intending to limit any aspect of the disclosure by any theory as to the underlying mechanisms responsible for the phenomena observed, LDOAM radiation used in the present disclosure induces a lowering of lipolytic enzymatic transition states in lipolytic enzymatic reactions and beneficially alters the normal cell thermodynamics at the membrane level, and potentially up-regulates cellular enzymatic processes. In other words, LDOAM affects molecules that mediate cellular mechano-transduction including, but not limited to, the lipid bilayer of the plasma membrane, the extra cellular membrane (ECM), transmembrane "integrin receptors", and cytoskeletal structures. Even if this modulation occurs by a small amount, the resulting physical force on the membrane could significantly alter cellular function and to a greater extent tissue mechanics. This is accomplished without generating substantial heat effects, and is a significant improvement over the background art, that simply relies on the effects of heat from a laser or other light source.

In contrast to LDOAM, other optical energies that have considerably less of a ratio of ($\mu s/\mu a$) than about 40 in the skin (dermis) above the adipose tissue, are less than optimal for absorption by fat cells and/or in modulating cellular mechano-transduction mediators. These wavelengths (because of less than optimal $\mu s/\mu a$ ratios) will generally lead to energy absorption in the dermis above the adipose tissues, and can heat these dermal tissues to a point that is injurious to the skin, and/or, via absorption, prevent the energy from getting to the subcutaneous adipose tissue.

Human Skin

Human skin is primarily made up of water and collagen. Collagen accounts for approximately 25% of all protein in humans, and it provides about 75% of the dry weight and about 18-30% of the volume of the dermis, which itself constitutes about 15-20% of the weight of the human body.

At many different laser wavelengths, only a single tissue constituent (e.g., water or collagen) absorbs incident radiation. Therefore, understanding the spatial characteristics of the collagen and water "spheres of influence" within dermal tissue is fundamental to understanding optical energy-transfer mechanisms through the dermal layer, and to the subcutaneous adipose tissue. In fact, because of these spatial characteristics of collagen and water within dermal tissue, the actual distribution of optical energy that penetrates the dermis to the subcutaneous fat may be controlled by more than one influence, the most important influences being:
1) the incident radiant exposure;
2) the optical absorption and scattering properties of the tissue itself; and
3) the "spot size" (or beam waist diameter, e.g., expressed in terms of full-width have maximum or 1/e powers) of the incident beam.

All three parameters are important to determine energy penetration through the skin to the subcutaneous fat, as are the absorptive chromophores of collagen and water. When one is dealing with biomedical Tissue Optics, tissue absorption coefficients may be used to express the optical absorption properties of a given tissue element, and may be designated as $\mu a$. The optical absorption properties of the skin are dominated by the absorption of proteins (collagen), melanin, hemoglobin, and water.

Figure 3:
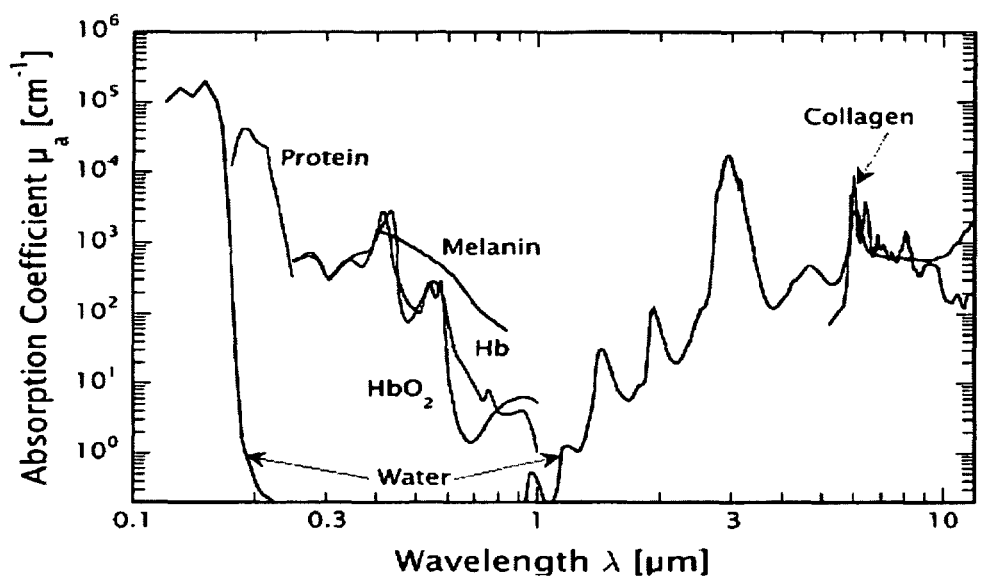
FIG. 3 is a diagram showing the optical absorption properties of the skin dominated by the absorption for protein (collagen), melanin, hemoglobin, and water.

Nevertheless, as shown in FIG. 3, there may be significant differences in individual chromophores (absorptive elements) within a tissue. Hence, it is postulated that the absorption coefficient of the tissue through which the radiation is traveling is an important factor in determining energy penetration through the skin to the subcutaneous fat.

Both optical absorption and scattering play significant roles in determining the optical spatial distribution of energy density deposited by a radiation source to subcutaneous adipose tissue. If the scattering component of the equation is negligible or absent (i.e., fat or water was being irradiated alone), the optical penetration depth of the incident radiation (the reciprocal of the absorption coefficient) would itself define the depth to which a given tissue was irradiated and heated.

However, at wavelengths where optical scattering in overlying tissues is significant, the optical penetration depth may be smaller than the reciprocal of the absorption coefficient, and also may be dependent on the diameter of the beam spot size. Optical scattering in tissue may take place because of the spatial differences in the refractive index within tissue. These differences may be dependent on factors that include, but are not limited to: the composition, size, and morphology of both cellular and extracellular tissue components. Because collagen-based tissues like the skin possess vast amounts of collagen fibrils that have significant variability in diameter (30-300 nm), orientation, and spacing, considerable optical scattering occurs.

Therefore, the scale and degree of optical absorption in the skin relative to optical scattering in the skin (defined by wavelength) is a key value used to determine the spatial distribution of radiation generated by the light source that will translate into a safe fluence to selectively irradiate subcutaneous adipose tissues and potentially augment and/or suppress a cell's existing biochemical processes.

If absorption is dominant over scattering in a tissue, the application of the Beer-Lambert law is appropriate to determine the spatial distribution of the absorbed radiation in a tissue from a known absorption coefficient of a particular wavelength. However, when scattering is the prevailing phenomenon, or scattering is equivalent to a wavelength's optical absorption in a tissue, a more detailed model of radiative transport such as those including Monte Carlo effect analysis may be used to obtain the desired distributions of the absorbed radiation of particular wavelengths.

Because subcutaneous fat begins at a depth of approximately 4 mm or greater into a patient's skin, and may be deeper for some individuals or some body areas, the following logic for choosing the correct wavelength is applied:
(1) far greater energy is needed (Power density and Energy Density) for the radiation to be transmitted to the subcutaneous fat causing selective heating or destruction at the mid-infrared peaks of 1150 nm and 1230 nm; and (2) the $\mu s/\mu a$ ratio are 20 and 8, respectively for these wavelengths and will be more heavily absorbed in the skin. See FIG. 4.

Figure 4:
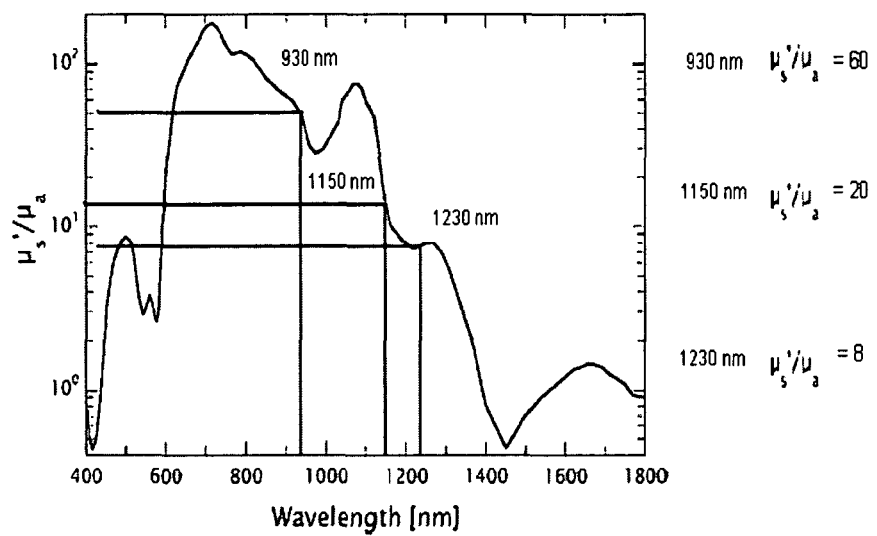
FIG. 4 is a diagram presenting the ratio of the scattering coefficient ($\mu s$) over the absorption coefficient ($\mu a$) in human skin of optical radiation from about 400 nm to about 1800 nm; optical radiation at the three near infrared wavelengths that have the highest absorption in adipose tissue or fat are emphasized.

Therefore a ratio of $\mu s/\mu a$ of at least about 40, as shown in FIG. 4, is desirable for the energy to be able to pass through several millimeters of tissue formed primarily of collagen and water, i.e., the skin (the μs/μa ratio of at least 40 primarily applies to light skins and may not necessarily work optimally for dark skin, i.e., darker than Fitzpatrick type 4 skin). Consequently, wavelengths in the bands of about 850 nm to about 879 nm and about 900 nm to about 939 nm (μs/μa approx=60 to 70) may be optimal as they are also absorbed in necessary chromophores (to effect biochemical modulation of existing enzymatic processes) within the adipocyte, without having undesirable thermal consequences in the skin.

When these wavelengths are coupled to a beam spot area of about 1.13 cm² or larger, they may also make use of the phenomena of Monte Carlo effects, to achieve optical tissue penetration through the skin and into the adipose tissue with less energy than is necessary to significantly heat up the system. This approach (μs/μa approx=60 to 70, Low Dosimetry (non-thermal), and Large irradiation area greater than 2 cm²) may be used to penetrate the dermal layer and allow absorption of enough optical energy at the selected wavelengths in the adipose tissue, and more specifically adipocyte membrane, to effect Low Dosimetry Optical Adipose Modulation or LDOAM with minimal heat deposition. This may be accomplished on large areas of dermal tissue above subcutaneous adipose tissue with Power Densities (W/cm²) and Energy Densities (J/cm²) that will not significantly heat up the system being irradiated by more than about 5 degrees Celsius in the adipocytes and/or the adipose tissue.

A significant parameter for successful adipose treatment with the present disclosure is the internal fluence distribution (exposure) in the adipose tissue being irradiated with about 930 nm or about 870 nm, which is made possible by the favorable μs/μa ratio in the overlying skin, and the large irradiation spot size. According to the LDOAM techniques of the present disclosure, Monte Carlo tissue simulations with near infrared energy forecast that as an irradiation spot size becomes "broad-beam" (1.2 cm or larger equivalent to an area of 1.13 cm²), and if the energy profile is a flat field (top-hat effect vs Gaussian), the optical energy will achieve a higher fluence distribution in the adipose tissue with the formula, than would be achieved with an irradiation spot of less than 1.2 cm, on the overlying skin.

During a treatment with a LDOAM device, in accordance with the present disclosure, the area of tissue to be treated is defined not simply as the tissue under the optimal beam, i.e., (pi×(radius)²), but as the treatment volume, i.e., (pi×(radius)²×depth), of the adipose tissue, because the fluence (Energy Density) in the adipose tissue is actually increased with the larger spot sizes and surface areas of irradiation.

Figure 5:
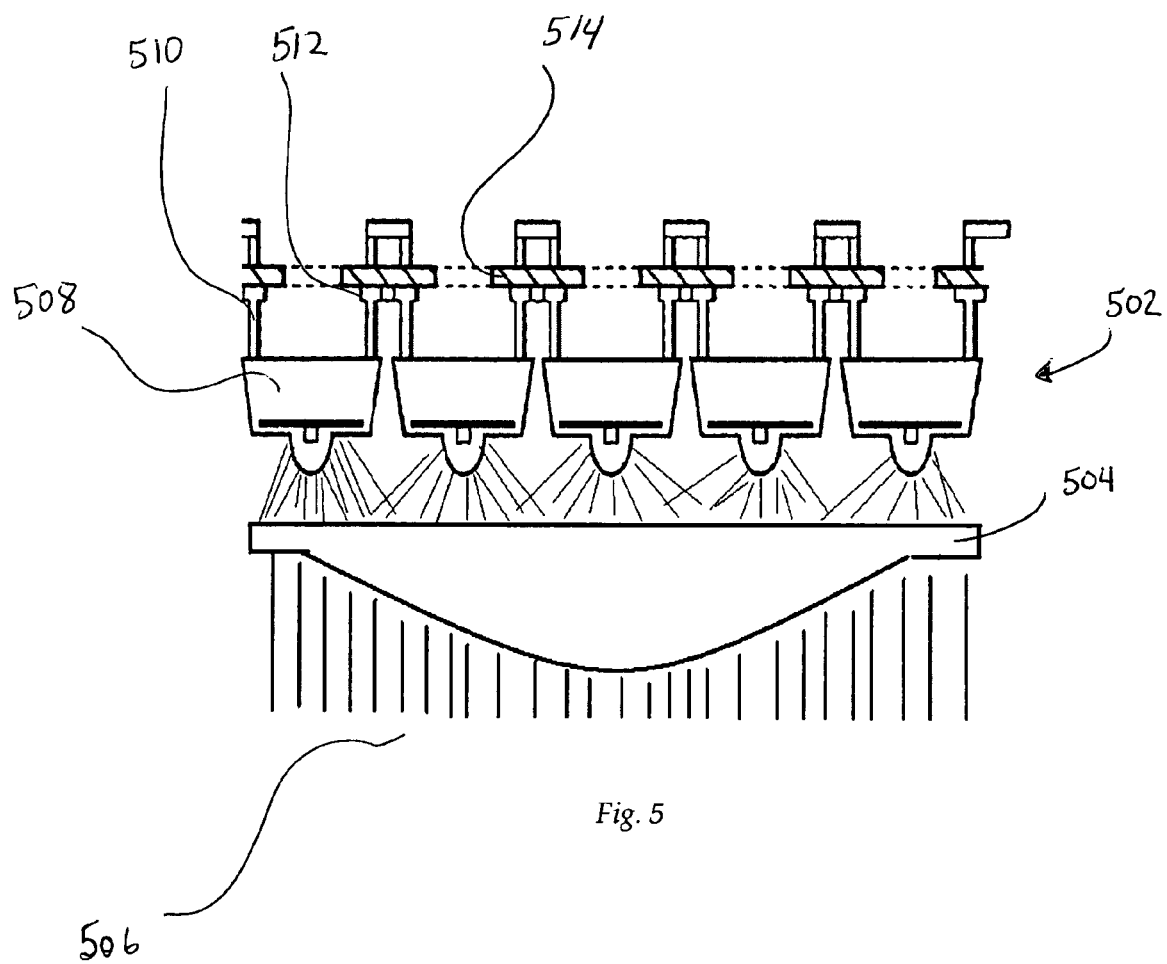
FIG. 5 is a perspective view of an LED array above a collimating lens, in accordance with the disclosure.
Figure 6:
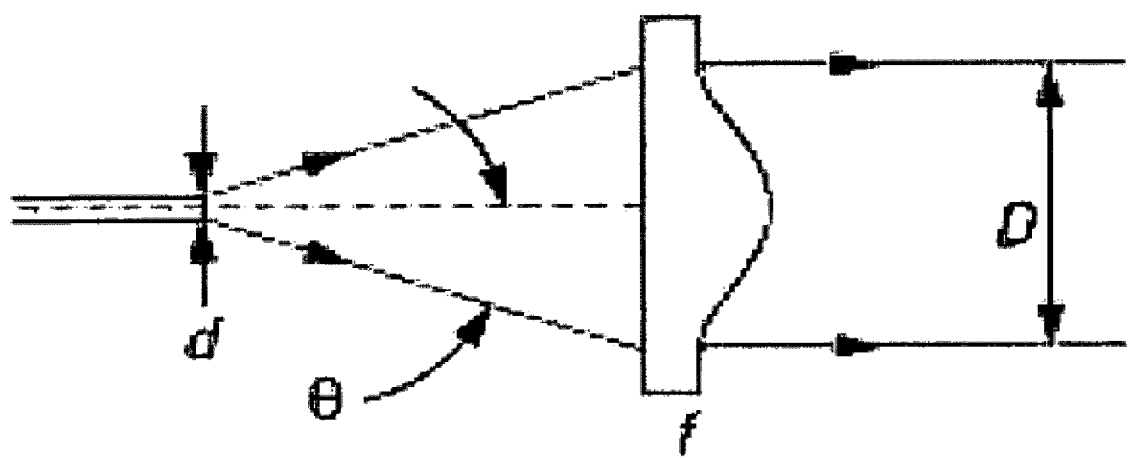
FIG. 6 is a perspective view of optical energy being collimated with a collimating lens having a short focal length.

As shown in FIG. 5, and according to the present disclosure, the output power of the LED array will be of a level such that the Power Density (W/cm²) of the Incident collimated spot will be of a large enough size (generated for example with a short focal length aspheric lens) to cause the distribution of optical energy that penetrates the dermis to be of greater fluence at the depth of the adipose tissue than it is at the surface of the skin. FIG. 5 illustrates an array of LEDs 502 assembled behind an aspheric lens 504 generating a collimating beam 506 with various diameters. Each LED consists of an LED assembly 508 connected to a power conduit by pins 510 and 512. Aspheric lens 504 is designed to refract light at large angels without introducing any significant spherical aberrations. It can have much shorter focal lengths than a comparably sized spherical lens. Because an aspheric surface minimizes the aberrations experienced by rays traveling through the outer circumference of a lens, it is specially useful for short focal length applications. Aspheric lens 504 may have a desired shape (e.g., elliptical, parabolic, hyperbolic, etc.) and/or optical prescription. Accordingly, aspheric lens 504 may be used to modify or control output intensity from the light source(s) to conform to a desired intensity distribution, e.g., a top-hat distribution, at a target site. In doing so, collimating lens 504 can accommodate or correct angular divergence disparities (aspect ratios) in the optical output of the light sources used, e.g., LEDs 502. In certain embodiments, (e.g., as shown in FIG. 6) arrays of suitable light sources (with or without collimating lenses) may be used in conjunction with (e.g., embedded, attached to, or placed in, etc.) a wrap or bandage that is conformable to a desired target surface, e.g., such a portion of a person's body. Accordingly, LDOAM radiation at LDOAM dosimetries can be applied to a person to treat (e.g., modulate biological processes in) adipose tissue.

This Fluence (Energy Density) distribution to the adipose tissue under the skin can therefore be maintained with less energy and power while avoiding any significant thermal rise in the area. Hence, safe and practical adipose biochemical modulation can occur with these accomplished parameters. The methods and device of the disclosure provide that:

1) The internal fluence distribution to the adipose tissue is greater than the surface fluence to the skin;
2) The illumination zone of treated adipose tissue given by (pi×(radius)²×depth) will be generated by large collimated irradiation spots to make use of known Monte Carlo effects of Optical Energy Tissue distribution phenomena; and
3) With larger spot sizes, the treatment area (adipose tissue) is defined by the area of tissue volume under the beam where the fluence (Energy Density) is higher than the incident (surface) Energy density, via Monte Carlo forecasts and calculations.

Figure 7:
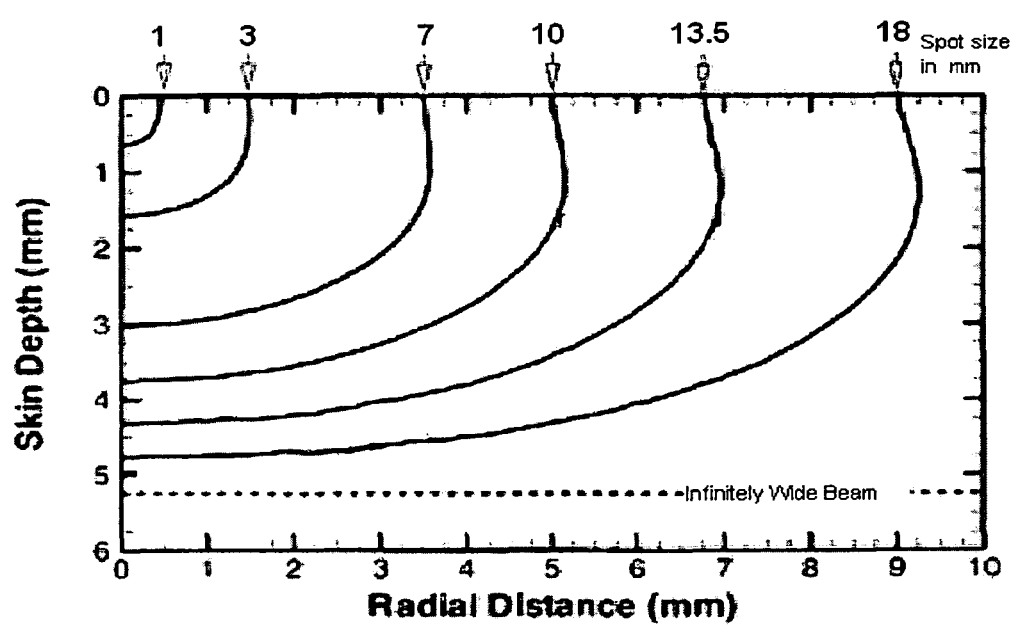
FIG. 7 is a graph presenting the effect of spot size (beam diameter) on illumination zone fluence and skin penetration.

The graph shown in FIG. 7, represents the effect on illumination zone fluence and tissue volume that is generated by optical spot size. Data is represented by Monte Carlo isofluence lines. Here, it can be further seen, that where treatment would begin at 12 mm spot sizes up to a theoretical "infinite spot size," that a spot of about 1.2 cm produces tissue fluence (deeper in the treatment zone) at approximately 75% that of the theoretical infinite spot size.

In contrast, the smaller spot sizes available with conventional fibers and optics, such as lasers, must increase fluence substantially greater than that generated by the present disclosure to produce adequate tissue penetration to the depth of the adipose tissue, and would thermolyze and/or burn tissue or porate adipocyte membranes, an effect that is not desirable.

The LDOAM techniques according to the present disclosure can provide radiation dosages at predetermined power densities and exposure times that thermodynamically lower enzymatic transition states of necessary enzymes in the adipocyte, via the absorption of optical energy at a selected wavelength of about 850 to about 879 nm, preferably about 870 nm and/or about 900 to about 940 nm, preferably about 930 nm in the lipid bilayer, and in the lipid pool, hence altering and modulating vital biochemical pathways in these cells. This is occur during periods of sport or exercise and is desired to facilitate adipocyte reduction and shrinkage.

The LDOAM treatment parameters are specified in terms of the average single or additive output power (milli-Watts) of the LED array, a filtered incandescent lamp, or other suitable light sources, at wavelengths of about 870 nm and about 930 nm. This information, combined with the area of the irradiation at the treatment surface being selected, will govern the calculations for effective radiation dosimetry and safe treatment of a given area and volume of tissue or cells.

For all laser stimulatory effects, the dosimetry used in the present LDOAM method and device is significantly less than that used to optically harm mammalian and/or bacterial cells, but enough to target and stimulate the previously discussed molecular endogenous LDOAM targets (e.g., cell membranes, lipid pool) in mammalian adipocyte cells in a beneficial fashion to enhance a given desired therapy.

According to one aspect of the present disclosure, the therapeutic system includes an optical radiation generation device adapted to generate LDOAM optical radiation, a delivery assembly for causing said optical radiation to be transmitted through an application region, and a controller operatively connected to the optical radiation generation device for controlling the dosage of the radiation transmitted through the application region, such that the time integral of the power density of the transmitted radiation per unit area is below a predetermined threshold.

According to one embodiment of this aspect of the disclosure, the LDOAM optical radiation generation device may further be configured to generate optical radiation substantially in either or both LDOAM wavelengths (about 850 to about 879 nm, preferably about 870 nm and/or about 900 to about 940 nm, preferably about 930 nm). The therapeutic system may further include a delivery system for transmitting the optical radiation in the second wavelength range through an application region and a controller operatively for controlling the optical radiation generation device to selectively generate radiation substantially in the first wavelength range or substantially in the second wavelength range or combinations thereof.

According to a further embodiment, the controller of the therapeutic system includes a power limiter to control the dosage of the radiation. The controller may further include memory for storing patients' profile and a dosimetry calculator for calculating the dosage needed for a particular patient based on the information input by a physician.

The optical radiation can be delivered from the therapeutic system to the application site in different patterns, such as, for example, in a single wavelength pattern or in a dual-wavelength pattern in which two wavelength radiation are multiplexed or transmitted simultaneously to the same treatment site. Alternatively, the radiation can be delivered in an alternating pattern, in which the radiations in two wavelengths are alternatively delivered to the same treatment site. The interval can be one or more pulses.

By employing a dual wavelength LDOAM method and device, the wavelengths are extraordinarily selective substantially at about 870 nm and about 930 nm, and are used at significantly lower energy levels than are needed to raise membrane temperatures to the point of causing damage to the membrane of the healthy adipose cells.

With the therapeutic methods, device, and system according to the present disclosure, unwanted thermal injury to healthy tissue can be prevented in the site being irradiated (undesired adipose tissue) by maintaining the radiance (joules/cm$^2$) and/or exposure time to a limit of defined parameters. These defined parameters are easily programmed into a control system by way of a programmed dosimetry calculator included in the system.

Figure 8:
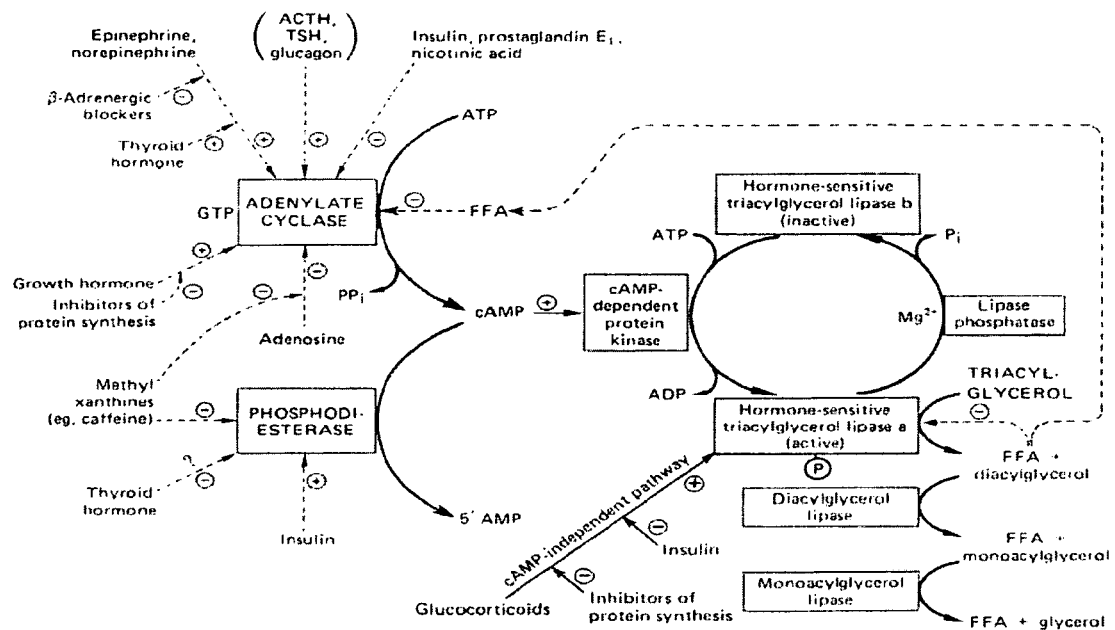
FIG. 8 is a diagram depicting various biochemical pathways and factors involved in the control of adipose tissue lipolysis.

The LDOAM method and device and system of the present disclosure may, in addition to augmenting and suppressing biochemical lipolysis and lipogenesis, respectively (as shown in FIGS. 1, 2, and 8) and increasing Leptin production, have one or more of the following whole body effects:

a) reduction of whole body insulin resistance, thereby
b) decreasing diabetes mellitus,
c) decreasing hypertriglyceridemia,
d) decreasing levels of high-density lipoprotein cholesterol,
e) increasing levels of low-density lipoprotein cholesterol,
f) increasing levels of adiponectin,
g) decreasing C-reactive protein,
h) decreasing interleukin-6, and
i) decreasing tumor necrosis factor (alpha).

Figure 9:
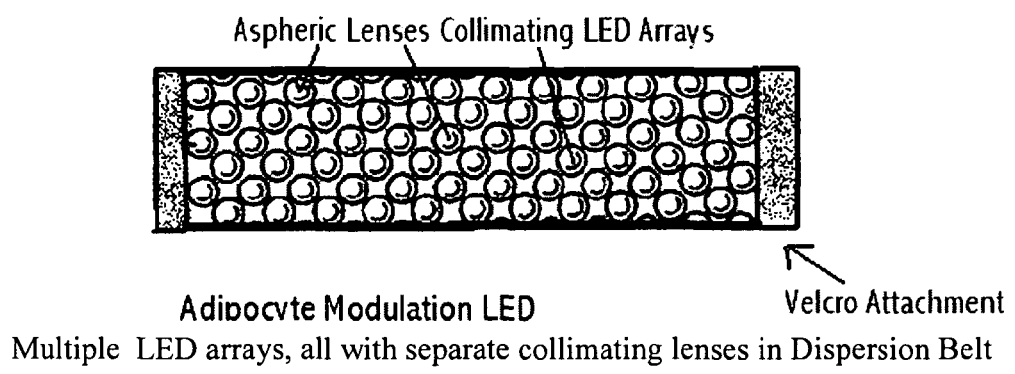
FIG. 9 is a view of multiple LED arrays wherein each LED has a separate aspheric collimating lens on a dispersion belt, according to the disclosure.
Figure 10A:
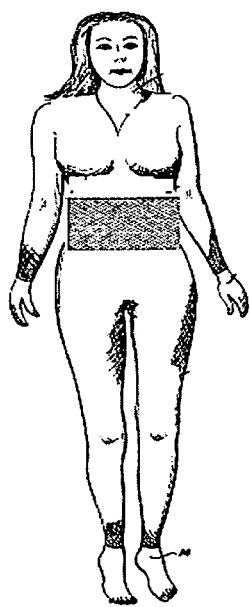
FIGS. 10A and B show an optical energy dispersion belt or bandage for use as a treatment to enhance the efficiency of fat metabolism during aerobic exercise or digestion. In 10B the LDOAM device is connected to a power supply, in accordance with the current disclosure.
Figure 10B:
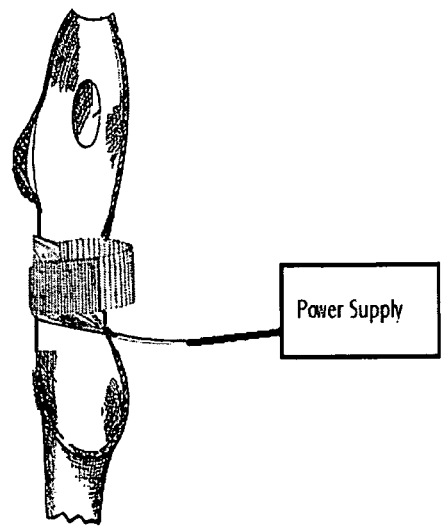
FIGS. 10C through E, each show an optical energy dispersion belt or bandage connected to a power supply during aerobic exercise, in accordance with the current disclosure.
Figure 10C:
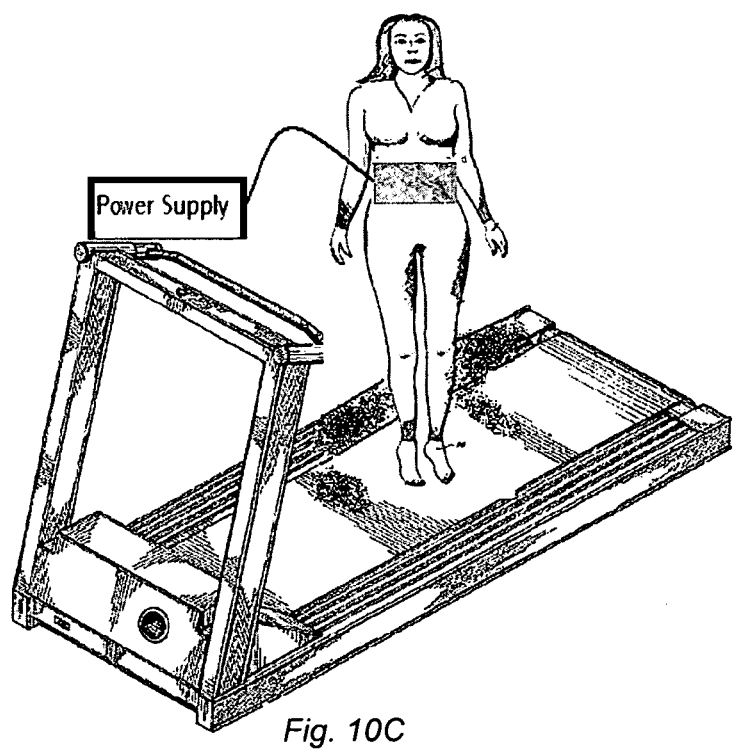
Figure 10D:
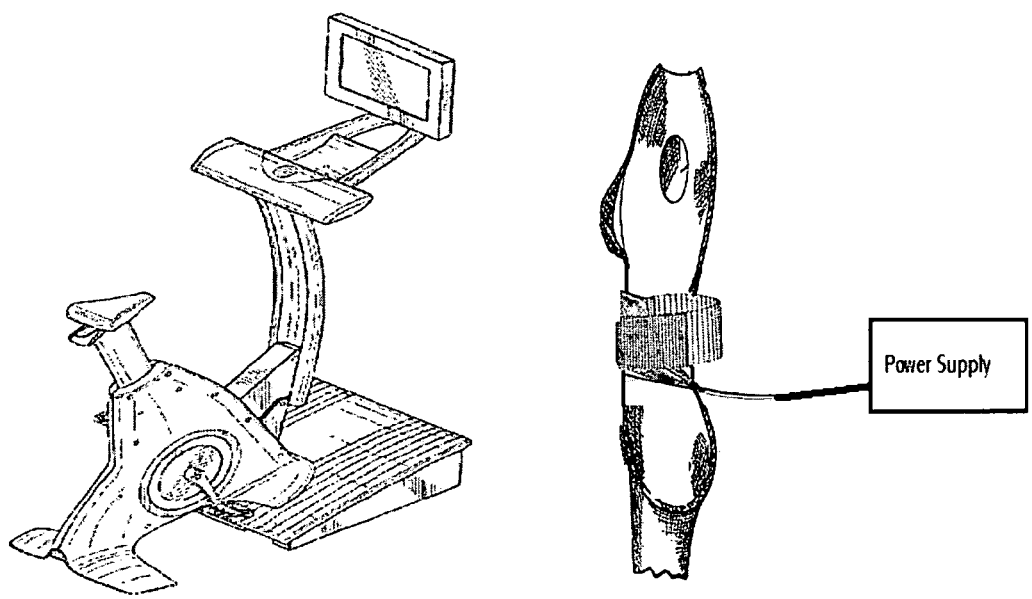
Figure 10E:
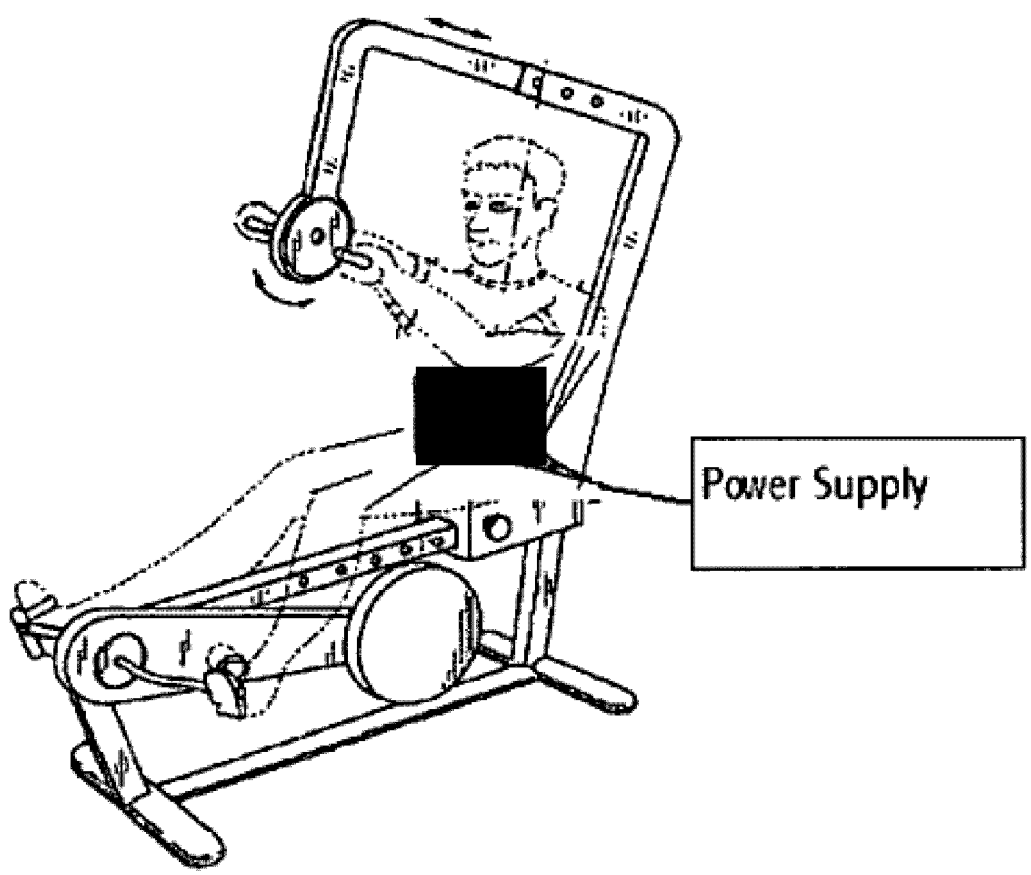

As shown in FIG. 9, the present device can be incorporated into or on an optical energy dispersion belt, bandage, or wrap, for example, for use as an adjunctive treatment of subcutaneous adipose optical bio-regulation to allow for large areas to be simultaneously treated with controlled optical dosimetry. Such an optical energy dispersion belt or bandage or wrap can be fabricated with multiple arrays of LEDs operative at the desired wavelength(s). In accordance with the present disclosure, each array can be collimated with a collimating lens of a short focal length (in one adaptation this would be an aspheric collimating lens, as seen in FIG. 6). This allows large areas of subcutaneous adipose tissue to be treated simultaneously during such activities as exercise, making use of Monte Carlo phenomena (i.e., large spot sizes) that modulate existing biochemical lipolysis and lipogenesis. Such collimating lenses can be configured and arranged as desired and may be used to produce a desired (e.g., flat top) intensity distribution, and may account for any beam output aspect ratio of the diodes used, which often have dissimilar angular divergence between orthogonal axes of beam output.

The present disclosure provides a method, device, and a system for reducing the level of fat or lipid in an adipocyte without significant generation of heat or intolerable adverse effects on the skin. In one embodiment, the method of the disclosure comprises the step of irradiating a target site with a first optical radiation having a wavelength band from about 905 nm to about 945 nm and/or a second optical radiation having a wavelength band from about 850 nm to about 879 nm at a dosimetry from about 0.015 W/cm$^2$ to 1 W/cm$^2$, to modulate innate biochemical processes of adipocytes in the target site. Preferably, the first wavelength band of the optical radiation ranges from about 925 to about 935. In accordance with one embodiment of the disclosure, each of wavelength bands may be irradiated alone or in combination with the other band, sequentially or in tandem. Preferably, the radiation bands are collimated when an incoherent light source is used to generate the above-mentioned wavebands.

In yet another embodiment of the disclosure, the biochemical processes modulated by the LDOAM dosimetry include, but are not limited to, lipolysis, lipogenesis, leptin production, and glucose absorption or metabolism. Preferably, these processes already are in progress, when LDOAM is used, either by sport and exercise activities or digestion and pharmacological means.

In another embodiment of the disclosure, LDOAM radiation is generated by light emitting diode (LED) arrays or by super-luminous LED arrays. Preferably, LEDs are arrayed with aspheric collimating lenses within a wrap.

The present disclosure further provides a device comprising a suitable optical light source such as LED arrays for generating LDOAM. In an embodiment, LED arrays with aspheric collimating lenses are assembled within an article of clothing. In yet another embodiment, such article of clothing has means for attaching to a power source and can be worn by a person while using a sport or exercise equipment to facilitate fat reduction.

According to a further aspect of the invention, an optical energy dispersion system for use as an adjunctive treatment of for subcutaneous adipose optical bio-regulation is provided, which allows for large areas to be simultaneously treated with controlled optical LDOAM wavelengths and dosimetry generated from multiple light emitting diode arrays (LEDs). See FIGS. 5 and 9. FIGS. 10A-E illustrate several embodiments of this aspect of the disclosure.

According to another embodiment of this aspect of the disclosure, there is provided an optical energy dispersion belt, bandage, or article of clothing for use as a treatment to enhance the efficiency of aerobic exercise, by augmenting lipolysis at the earliest possible point in moderate aerobic exercise, to allow for non-esterified fatty acid (NEFA's) to enter the blood stream to be used as metabolic fuel more efficiently than would occur without the disclosure. This would also maintain a high level of subcutaneous adipose lipolysis to aid in the preferential use of NEFA's for metabolic fuel. See FIGS. 10A-E.

Other Exemplary LDOAM Embodiments

About 90 minutes after a person finishes a meal, (i.e., the post-absorptive state) glucose metabolism in the individual will approach a steady state, where approximately 80% of all blood glucose will be taken up by various tissues. In this state, approximately 50% of the glucose is taken up by the brain, and 20% is absorbed by the red blood cells. As a general rule, muscle and adipose tissue together only absorb the remaining 20% of total glucose utilization.

Enzymatic Activation Energy

Figure 11:
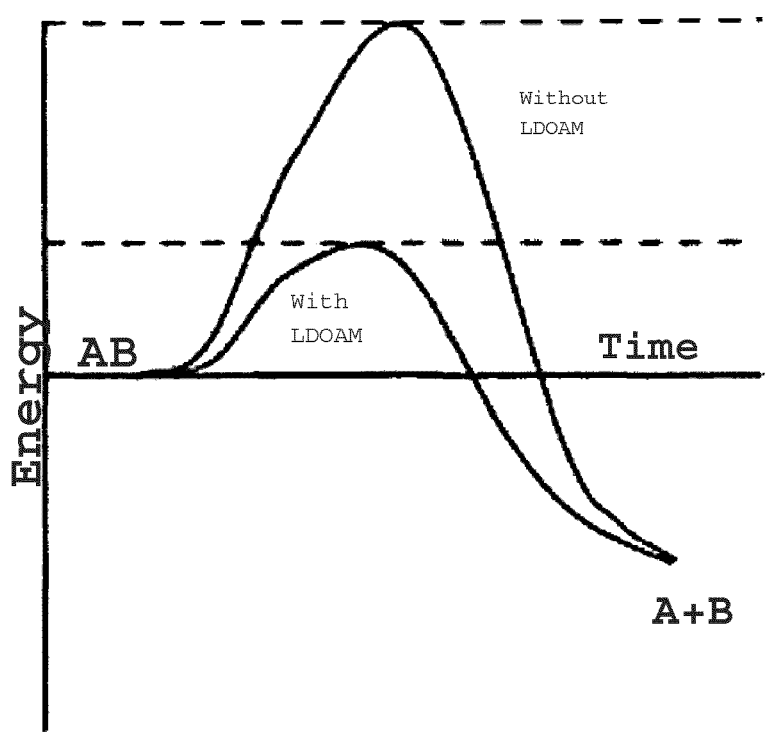
FIG. 11 is an exemplary diagram showing that the activation barrier to a biochemical reaction (such as lipolysis) can be lowered by using a radiation with the wavelength of about 870 and/or about 930 nm at the defined dosimetry.

It is shown, for example, in the graph in FIG. 11, that if the activation barrier to a biochemical reaction (such as lipolysis) can be lowered through the use of the present disclosure. The addition of free energy (at defined wavelengths and dosimetries) may prospectively cause the necessary reactants to have a greater potential energy (vibration). This allows these reactants to more easily position themselves in the enzymes active sites in the membranes, for the enzymatic reaction of lipolysis. This can occur by making the formation of an enzyme mediated transition state more frequent, thus decreasing the activation energy of the reaction, and causing a faster reaction rate.

Many of the complex enzymes associated with the plasma membrane of the adipocyte are tightly bound to it in a variety of ways. Transmembrane proteins have their polypeptide chains passing completely through the lipid bilayer. In the midst of the membrane (lipid bilayer) associated proteins, the segments of the proteins within direct proximity of the lipid bilayer consist primarily of hydrophobic amino acids. These specific proteins are usually arranged in what is known as an alpha helix, so that the polar —C=O and —NH groups at the peptide bonds can interact with each other, rather than with their hydrophobic surroundings. In contrast, the fraction of the proteins that project out from the membrane have a predisposition towards elevated percentages of hydrophilic amino acids.

It is known that the composition of human adipocyte plasma membranes is mainly made out of phosphatidylcholine and phosphatidylethanolamine, with sphingomyelin, phosphatidylserine, and phosphatidylinositol being less abundant. More importantly, the mean value of the total protein content of the adipcyte membranes is reported to be approximately 50% by dry weight.

The present method selectively targets these unique hydrocarbon (lipid) chains of the bilayer of the plasma membranes of adipocytes, and may alter the static orientational order of the membrane lipid bilayer, with directly absorbed (milliWatt) energy, to optically force changes in the membrane, causing dynamic interactions of the bilayer. This concomitant transduction then leads to conformational (structural) changes in the membrane bound proteins that catalyze and modulate adipocyte processes such as lipolysis. These processes can be altered by things like physical forces on the membrane, minor changes in the extracellular matrix (ECM) that the eukaryotic cell resides in, and any changes in the basic cell structure. The molecular mechanism by which a cell senses and responds to external mechanical stress has been referred to as "cellular mechanotransduction".

The molecules that mediate cellular mechanotransduction include the lipid bilayer of the plasma membrane, the ECM, transmembrane "integrin receptors", and cytoskeletal structures. Therefore, any external stimulus or device that may cause optical interference with the normal cell membrane thermodynamics (without generating substantial heat effects) and hence cause cellular mechanotransduction to the plasma membrane and biochemical pathways, is considered novel and an improvement of the prior laser art, that simply relies on the effects of heat from a laser.

Hence, if the lipid bilayer actively absorbs milli-watt photon energy at about 870 and/or about 930 nm, for example, causing increased kinetic interactions on a molecular level in the molecular bonds that make up the membrane (but in the absence of a significant temperature increase) the membrane will appreciate free energy addition and mild mechanotransduction forces that could significantly alter cellular function and to a greater extent the adipose organ being irradiated.

Minute mechanical forces can regulate a cells biochemical activity in a manner that is equally as potent as chemical or pharmacological signals. This means that slight deformations in a cell membrane (because of the increased kinetic energy associated in the lipid bilayer of the cell membranes with about 870 nm and/or about 930 nm optical absorption) can and will cause remarkable conformational changes to the vital trans-membrane proteins. This could be a direct ramification of cellular mechanotransduction via the increased kinetic energy of the C—C and C—H bonds in the lipid bilayer from 930 nm optical energy absorption.

It is believed that as the lipid hydrocarbon component of cell membranes absorb the wavelength about 870 and/or about 930 nm infrared energy in the carbon-hydrogen bonded chains at correct dosimetry to effect change (but below deleterious thermal dosimetry), that kinetically driven events could alter the molecular dynamics of membrane-bound proteins (such as trans-membrane Adenylate Cyclase) through significantly increased molecular motions of the lipids in the membrane as they absorb energy from the LDOAM system. Because even a small chemical shift in the lipid bilayer (such as reduced packing constraints or distance between the lipids) could be enough to change the molecular shape of an attached respiratory and/or transport protein (along with the thermodynamics and kinetics of the enzyme), and render it more active, the LDOAM system is potentially a powerful tool for modulation of biochemical processes in adipocytes.

These events are believed to be unique to the LDOAM system, and are not at all reflective of the large infrared bands claimed, or far larger dosimetries needed for thermal interactions revealed in the prior art.

As postulated by the present inventor, and without being bound by any theory of operation, if the wavelength about 870 nm and/or about 930 nm near infrared energy is preferentially absorbed by long chain C-H molecules, and these long chain C-H molecules are the basis of the phospholipid bilayer of cell membranes, it would take very little alteration in the local environment of one of these proteins (sitting within the membrane) to change its 3-D conformational shape, and hence modulate or augment its function. If this conformational change occurs, causing/influencing enzymatic action, increased lipolytic activity could also occur. The mechanism postulated above has been corroborated to an extent by data presented through the inventors experimental in vitro designs, described herein.

The present inventor tested human adipocytes that were plated into selected wells of 24-well tissue culture plates for selected LDOAM experiments at given dosimetry parameters. The plates were inoculated with isoproterenol immediately before irradiation to initiate biochemical lipolysis in all treatment and control wells, and the products of lipolysis were measured as glycerol and fatty acid concentrations outside of the cells.

These experiments showed that under specific irradiation protocols with the 930 nm wavelengths, that there was a significant augmentation of biochemical lipolysis (above the non-irradiated controls), without a concomitant temperature increase of the experimental model, once lipolysis was initiated with Isoproterenol.

It has been reported in the literature that the maximum lipolytic response to isoproterenol is limited by the accumulation of cyclic AMP and, that a plot of log cAMP vs. glycerol release (during lipolysis) results in linear relationship as the level of cAMP rises.

Adenylate Cyclase is the enzyme that catalyzes the formation of cylic AMP from ATP. This enzyme is vitally important in many areas of Eukaryotic Signal Transduction. Adenylate cyclase can be activated or inhibited by the G proteins that are coupled to plasma membrane receptors and are thus able to respond to hormonal or other stimuli.

Therefore, without wishing to be bound by any theory and not intending to limit any aspect of the disclosure by any theory as to the underlying mechanisms responsible for the phenomena observed, it is postulated that the wavelengths irradiated according to the present methods and systems are absorbed by the adipocyte cell membranes, and effect the transmembrane Adenylate Cyclase enzyme, increasing the level of intracellular cAMP through a mechanism of optically mediated mechanotransduction, that then upregulates or forward modulates the distal lipolytic cascade of enzymes to produce more products of lipolysis (Glycerol and FA).

Photochemistry, Photophysics and Phototherapy

The First Law of Photochemistry (and photophysics) states that photons must first be absorbed for photochemistry (or photophysics) to transpire. As photobiological and phototherapeutic effects are initiated by photochemistry (or photophysics), no photochemistry (or photophysics) will occur, unless a particular wavelength of light is absorbed by a biological system. This is true independent of the length of time that one would irradiate a system with a non-absorbed wavelength of light. A number of studies in the prior art have not taken into account this "First Law of Photochemistry (and photophysics) in publishing the results in the literature.

The absorption spectrum of a given wavelength of light is a plot of the probability that the photons (of the given wavelength) will be absorbed by the biological system being irradiated. As each chemical compound in a biological system has a different absorption spectrum, because of its unique electronic structure, every individual wavelength that is absorbed by a chemical compound will be absorbed to different degrees.

Once a given photobiological response is observed, the next step is to develop and determine the optimum dose of the wavelength of radiation needed to produce the desired photobiological effect, and establish what is called the action spectrum. The action spectrum is a plot of the relative effectiveness of different wavelengths of light (at different dosimetries) that will cause a particular biological response. Therefore, the action spectrum not only identifies the wavelengths that will have the maximum desired biological effect with the least dose of radiation, but also identifies the molecular target of the radiation.

When a photon of light is absorbed by a molecule, the electrons of that molecule are raised to a higher energy state. This (now) excited molecule then must lose the extra energy that the photon provided. With near-infrared wavelengths, this generally occurs by the vibrating molecules giving off heat. The Photobiological responses of augmented lipolysis are the result of photochemical and/or photophysical changes produced by the absorption of the LDOAM non-ionizing radiation.

The inventor's studies have demonstrated that the degree of the phototherapy effect depends on the physiological state of the adipocytes at the instant of irradiation. For example, when irradiating adipocytes that were not undergoing lipolysis at Energy Densities from 8 J/cm$^2$ to 4000 J/cm$^2$, the effect of the irradiation on the adipocytes was minimal or nonexistent. In such testing, only after lipolysis was initiated with the drug Isoproterenol (to mimic moderate exercise) the phototherapeutic effect of augmented Lipolysis was observed with 10-20 J/cm$^2$ irradiation at about 930 nm, and 20.4 J/cm$^2$ at about 870 nm.

It has also been shown that there may be no significant difference whether the light used for Biostimulation and/or phototherapy is generated by a laser or from non-coherent light of the same wavelength (i.e., filtered incandescent lamp or LED).

Phototherapy of adipocytes—whether using about 930 nm and/or about 870 nm low-intensity radiation in from a laser, an LED, or a filtered incandescent lamp—can potentially be beneficial in a number of clinical situations, as an augmentation to exercise and weight-loss.

As was described, about 870 nm and/or about 930 nm energy may be actively absorbed in the molecular bonds of the lipids, in the lipid pool of the adipocyte that in turn causes increased kinetic interactions on a molecular level of the fatty acid substrates for lipolysis. These increased kinetic interactions caused by the absorption of photons of about 870 nm and/or about 930 nm may immediately be converted to vibrational and rotational energy within the fatty acid molecules which is the molecular basis for heat. However, as will be evident with the dosimetric range involved for augmented lipolysis to be achieved with the LDOAM system, there is not sufficient energy density (Joules/cm$^2$) added to the lipid pool of the adipocyte to raise the temperature by the required amount to inhibit lipolysis. Also, on the extreme end of the background art with other laser wavelengths, photothermolysis (heat induced death) of adipocytes with near infrared laser energy has been implemented with significantly larger energies and temperature increases. Much of the prior art desires the destruction of adipose tissue thermally, for its surgical removal, which is not the method or intent of the present disclosure.

Another example of potential Low Level enzymatic stimulation with about 870 nm and/or about 930 nm of the adipocyte can occur through the cellular cytoskeleton. In mammalian cells, the cellular organelles, nuclei and most importantly the cell membrane lipid bilayer are interrelated and organized by a comprehensive series of cytoskeletal filaments. Many of these are also connected linked with ECM molecules by means of specific receptors on the outside of the cell membrane that as transmembrane receptors are still connected to the cytoskeleton. The biochemical regulation of a cell's shape and function is mechanically controlled by the structural and functional geometry of these intra- and extra-cellular system in the cytoskeleton of mammalian cells including adipocytes.

The mammalian cytoskeleton is a highly integrated network of fibers, filaments and polymers all formed within the cell as part of normal function. Any mechanical modification of this network of cytoskeletal fibers (such as increase of kinetic energy from absorption of the wavelength about 870 nm and/or about 930 nm optical energy in an adipocyte pool or membrane) can alter the chemical environment of the cell, and potentially induce changes in cell shape, motility and metabolism, by changing the molecular dynamics of the cell.

The cytoskeleton is actively implicated in a range of cell functions that include force transduction and production, cell membrane modulation, hormone secretion, intracellular transport, organelle translocation, and cell migration. The cytoskeleton serves to provide a measure of mechanical stiffness to resist cell deformation in the face of forces like fluid flow dynamics, or mechanical stresses from surrounding tissues. Even though it has not been clearly explained how the physical mechano-transduction and concomitant deformation of a cell membrane protein or cytoskeletal component can lead to a given biochemical response, it has been suggested in many tissues that this network of filaments, once deformed, will change the membrane tension force in cells and alter things like mechano-sensitive ion and nutrient channels and enzymes.

The molecules that mediate cellular mechano-transduction include the lipid bilayer of the plasma membrane, the ECM, transmembrane "integrin receptors", and cytoskeletal structures. Therefore, any optical external stimulus or device that may induce a lowering of lipolytic enzymatic transition states in lipolytic enzymatic reactions will beneficially alter the normal cell thermodynamics at the membrane level, and potentially up-regulate cellular enzymatic processes.

Ability to Penetrate Beyond the Dermal Layer to Subcutaneous Adipose Tissue

Figure 12:
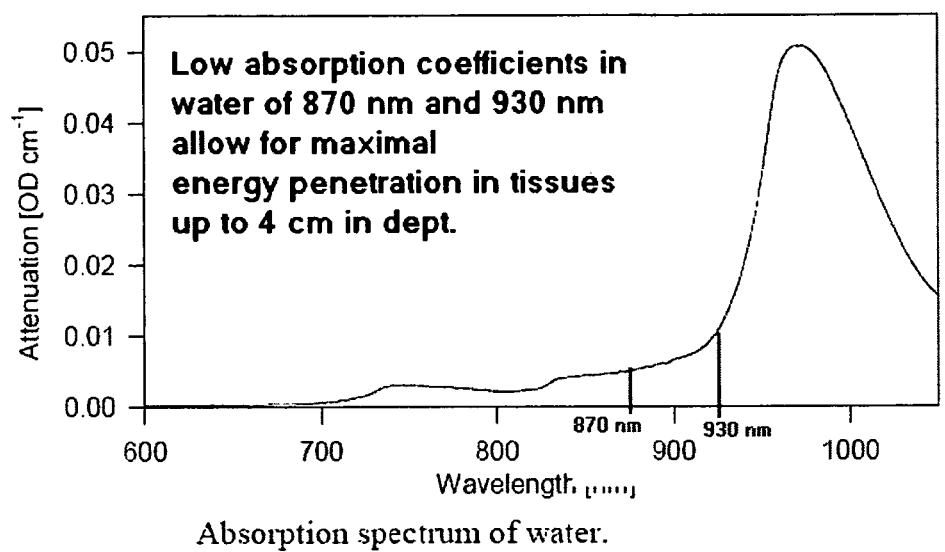
FIG. 12 is the absorption spectrum of water with maximum absorption being at about 950 nm.

The absorption spectrum of water has a therapeutic transmission window in the near-infrared until about 940 nm, then a sharp upswing to a peak at 980 nm. See FIG. 12. This allows the wavelength of about 870 nm and/or about 930 nm electromagnetic energy to pass through the dermal layer (about 85% water) and impact the adipose tissue directly under the skin.

Aerobic Exercise

Sub-maximal aerobic exercise is the best technique to maximize lipolysis and reverse obesity. A level from about 20% to about 40% Vo2 Max exercise intensity will causes a rise in the hormones epinephrine, norepinephrine, and growth hormone to inhibit the release of insulin from the pancreas. This hormonal environment enhances liver glucose output and promotes greater fat utilization and lipolysis.

A gradual loss of body fat comes about from burning more calories during exercise than one takes in through exogenous sources. In view of the fact that mild to moderate aerobic training (about 40% Vo Max) creates a metabolic environment that is advantageous for fat metabolism, there is a need in the art to increase the body's fat-burning proficiency (lipolysis) after initiating that mild to moderate aerobic exercise without increasing the negative feedback parameters to the lipolytic reactions, that are the significantly elevated temperature and epinephrine concentrations from intense exercise. Application of the present method during or following exercise increases fat metabolism and results in enhanced weight loss.

Increased Exercise Intensity and Decreased Lipolysis

Endogenous triacylglycerols characterize an important source of fuel for exercise. Lipolysis increases progressively during exercise, with the specific rate determined by energy requirements of working muscles, monoglyceride delivery to mitochondria in the working muscles, and the oxidation of other substrates such as glycogen. It is the catecholamine response to exercise that increases lipolysis in adipose tissue.

Alterations in lipolysis and fatty acid mobilization during exercise depend, in large part, on exercise intensity and core body temperature. Lipolysis is lower in high-intensity exercise, than in moderate-intensity exercise, in part because of increase epinephrine and heat in the system. For example, for the duration of exercise at about 65% peak pulmonary oxygen uptake ($VO_2$ peak), an increased core temperature will lead to increased carbohydrate oxidation during exercise and a concomitant decrease in lipolysis. This is caused by increased muscle glycogen use with no change in glucose uptake by the muscle It is also recognized the epinephrine concentrations are elevated during exercise in the heat compared with exercise in cooler environments. It has been confirmed that a 2-fold increase in circulating adrenaline increased muscle glycogen utilization, glycolysis and carbohydrate oxidation when subjects were exercising at about 70% peak pulmonary oxygen uptake (VO2 peak). The magnitude of the increase in adrenaline in that study was similar to those observed in previous studies that compared hot and thermo-neutral environments. Thus the increase in core temperature during exercise in the heat may also result in an increased adrenaline secretion.

Without wishing to be bound by any theory and not intending to limit any aspect of the disclosure by any theory as to the underlying mechanisms responsible for the phenomena observed, it is postulated that when a photon of light is absorbed by a molecule, the electrons of that molecule are raised to a higher energy state. This (now) excited molecule then must lose the extra energy that the photon provided. With near-infrared wavelengths, this generally occurs by the vibrating molecules giving off heat. The Photobiological responses of, for example, augmented lipolysis are the result of photochemical and/or photophysical changes produced by the absorption of the LDOAM non-ionizing near infrared radiation.

EXAMPLES

LDOAM Treatment Parameters for in Vitro Adipocyte Tests

The following parameters illustrate the methods according to the disclosure as applied to Human Adipocytes at thresholds well below thermal damage. Cultured human adipocytes were obtained from Zen-Bio Inc., North Carolina and used for in vitro experimentation. The adipocyte precursor cells (preadipocytes) were isolated from subcutaneous adipose tissue from elective surgery in healthy non-diabetic donors between 18 and 60 years old. The preadipocytes were isolated by centrifugal force after collagenase treatment, and then cultured as growing precursor cells. These cells were then differentiated into adipocytes using medium supplemented with adipogenic and lipogenic hormones. The process of differentiating preadipocytes to adipocytes is disclosed in U.S. Pat. No. 6,153,432.

Glycerol Assay

To assess lipolytic activity using the measurement of glycerol released into the medium is the method of choice, as the enzyme glycerokinase (to create glycerol from precursors) is not present in adipocytes. Glycerol released to the medium is phosphorylated by adenosine triphosphate (ATP) forming glycerol-1-phosphate (G-1-P) and adenosine-5'-diphosphate (ADP) in the reaction catalyzed by glycerol kinase. G-1-P is then oxidized by glycerol phosphate oxidase to dihydroxyacetone phosphate (DAP) and hydrogen peroxide (H2O2). A quinoneimine dye is produced by the peroxidase catalyzed coupling of 4-aminoantipyrine (4-AAP) and sodium N-ethytl-N-(3-sulfopropyl)m-anisidine (ESPA) with H2O2, which shows an absorbance maximum at about 540 nm. The increase in absorbance at about 540 nm is directly proportional to glycerol concentration of the sample. The glycerol assay kit was obtained from Zen-Bio Inc., North Carolina.

Free Fatty Acid Assay

Assessment of lipolytic activity was be detected through measurement of non-esterified fatty acids (NEFA) released by adipocytes. This colorimetric assay allows for direct Free Fatty Acidsin the media to form a purple product that absorbs light at about 550 nm. This allows the concentration of NEFA to be determined from the optical density measured at about 540 to about 550 nm. The NEFA assay kit was obtained from Zen-Bio Inc., North Carolina.

Leptin Assay

Assessment of Leptin production and secretion from the human adipocytes was completed with a quantitative sandwich enzyme immunoassay technique. A monoclonal antibody specific for Leptin was pre-coated onto a microplate, and standards and samples were pipetted into the wells where any Leptin present was bound by an immobilized antibody. After washing away any unbound substances, an enzyme-linked monoclonal antibody specific for Leptin was added to the wells. Next, following a wash to remove any unbound antibody-enzyme reagent, a substrate solution was added to the wells and a color developed in proportion to the amount of Leptin bound in the initial step. Finally, the color development is stopped and the intensity (optical density) of the color was measured. The Leptin Assay kit was obtained from R&D Systems, Inc., 614 McKinley Place N.E. Minneapolis, Minn. 55413.

Cell Cultures for Experiments

All human adipocytes were plated into selected wells of 24-well tissue culture plates for selected NIMEL experiments at given dosimetry parameters. The plates were inoculated with isoproterenol immediately before irradiation to initiate biochemical lipolysis in all treatment and control wells.

Following Optical Treatments with a NIMEL Laser System, the directions were followed for the Zen-Bio Glycerol and Fatty Acid Assay kits described previously Equivalent assay studies and incubation times were performed for all NIMEL irradiation tests with Human Adipocyte Cells in the in vitro tests. Data in set in bold represent actual change from control (non-irradiated) samples.

Example I

Dosimetry Values for Wavelength 870 nm In Vitro

The NIMEL single wavelength of about 870 nm demonstrates lipolysis suppression in vitro at the following dosimetry ranges.

TABLE I

| NIMEL OUTPUT POWER (W) 870 NM | BEAM SPOT 6 CM DIAMETER | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) |
|---|---|---|---|---|---|
| Plate 5 0.5 W | 28.26 cm$^2$ | 15 min 900 sec | 450 J | 15.3 J/cm$^2$ | 0.017 W/cm$^2$ |

| Plate | Time After Irradiation (min.) | Treated 1 | Control 1 | Control 2 |
|---|---|---|---|---|
| | | Glycerol Concentrations Gly Conc. (micro. M) | | |
| 5 | 30 | 35.3846 | 44.2308 | 43.4615 |
| 5 | 60 | 51.9231 | 62.3077 | 65.0000 |
| | | Free Fatty Acid Concentrations FFA Conc. (micro. M) | | |
| 5 | 30 | 241.5000 | 294.8333 | 254.0000 |
| 5 | 60 | 297.3333 | 427.3333 | 449.8333 |

| | Relative Glycerol Concentrations (Percent of control) | | | Relative Free Fatty Acid Concentrations (Percent of control) | |
|---|---|---|---|---|---|
| Plate | Time After Irradiation (Min.) | T1 % Cont | Plate | Time After Irradiation (Min.) | T1 % Cont |
| 5 | 30 | 81.42 | 5 | 30 | 95.08 |
| 5 | 60 | 79.88 | 5 | 60 | 66.10 |

The single wavelength of 870 nm demonstrates Lipolysis augmentation in vitro at the following dosimetry ranges.

TABLE I - A

| NIMEL OUTPUT POWER (W) 870 NM | BEAM SPOT 6 CM DIAMETER | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) |
|---|---|---|---|---|---|
| Plate 5 0.5 W | 28.26 cm$^2$ | 20 min 1200 sec | 600 J | 20.4 J/cm$^2$ | 0.017 W/cm$^2$ |

| Plate | Time After Irradiation (min.) | | Treated 1 | Control 1 |
|---|---|---|---|---|
| | Glycerol Concentrations Gly Conc. (micro. M) | | | |
| 5 | 15 | | 16.1538 | 5.0000 |
| 5 | 75 | | 30.0000 | 21.5385 |
| 5 | 135 | | 48.8462 | 25.7692 |
| | Free Fatty Acid Concentrations FFA Conc. (micro. M) | | | |
| 5 | 15 | | 49.0000 | 19.0000 |
| 5 | 75 | | 159.0000 | 69.0000 |
| 5 | 135 | | 207.3333 | 83.1667 |

| | Relative Glycerol Concentrations (Percent of control) | | | Relative Free Fatty Acid Concentrations (Percent of control) | |
|---|---|---|---|---|---|
| Plate | Time After Irradiation (Min.) | T1 % Cont | Plate | Time After Irradiation (Min.) | T1 % Cont |
| 5 | 15 | 323.08 | 5 | 15 | 257.89 |
| 5 | 75 | 139.29 | 5 | 75 | 230.43 |
| 5 | 135 | 189.55 | 5 | 135 | 249.30 |

Example II

Dosimetry Values for Wavelength 930 nm In Vitro

The single wavelength of about 930 nm demonstrates substantial lipolysis augmentation in vitro at the following ranges.

TABLE II

| NIMEL OUTPUT POWER (W) 930 NM | BEAM SPOT 6 CM DIAMETER | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) |
|---|---|---|---|---|---|
| Plate 6 0.5 W | 28.26 cm2 | 15 min 900 sec | 450 J | 15.3 J/cm$^2$ | 0.017 W/cm$^2$ |

| Plate | Time After Irradiation (min.) | Treated 1 | Control 1 | Control 2 |
|---|---|---|---|---|
| | Glycerol Concentrations Gly Conc. (micro. M) | | | |
| 6 | 30 | 51.9231 | 31.5385 | 46.1538 |
| 6 | 60 | 81.1538 | 52.3077 | 70.7692 |
| | Free Fatty Acid Concentrations FFA Conc. (micro. M) | | | |
| 6 | 30 | 510.6667 | 195.6667 | 138.1667 |
| 6 | 60 | 404.0000 | 254.0000 | 329.8333 |

TABLE II-continued

| | Relative Glycerol Concentrations (Percent of control) | | | Relative Free Fatty Acid Concentrations (Percent of control) | |
|---|---|---|---|---|---|
| Plate | Time After Irradiation (Min.) | T1 % Cont | Plate | Time After Irradiation (Min.) | T1 % Cont |
| 6 | 30 | 112.50 | 6 | 30 | 369.60 |
| 6 | 60 | 114.67 | 6 | 60 | 122.49 |

The single wavelength of about 930 nm demonstrates substantial Lipolysis augmentation in vitro at the following ranges.

TABLE II - A

| NIMEL OUTPUT POWER (W) 930 NM | BEAM SPOT 6 CM DIAMETER | TREATMENT TIME (SEC) | TOTAL ENERGY (JOULES) | ENERGY DENSITY (RADIANT EXPOSURE) ($J/cm^2$) | POWER DENSITY (IRRADIANCE) ($W/cm^2$) |
|---|---|---|---|---|---|
| Plate 3 0.5 W | 28.26 $cm^2$ | 20 min 1200 sec | 600 J | 20.4 $J/cm^2$ | 0.017 $W/cm^2$ |

| Plate | Time After Irradiation (min.) | Treated 1 | Control 1 |
|---|---|---|---|
| | Glycerol Concentrations Gly Conc. (micro. M) | | |
| 3 | 15 | 9.2308 | 3.0769 |
| 3 | 75 | 21.5385 | 12.6923 |
| | Free Fatty Acid Concentrations FFA Conc. (micro. M) | | |
| 3 | 15 | 21.5000 | 8.1667 |
| 3 | 75 | 59.8333 | 49.0000 |

| | Relative Glycerol Concentrations (Percent of control) | | | Relative Free Fatty Acid Concentrations (Percent of control) | |
|---|---|---|---|---|---|
| Plate | Time After Irradiation (Min.) | T1% Cont | Plate | Time After Irradiation (Min.) | T1% Cont |
| 3 | 15 | 300.00 | 3 | 15 | 263.27 |
| 3 | 75 | 169.70 | 3 | 75 | 122.11 |

Example III

Dosimetry Values for Wavelengths 870 and 930 nm In Vitro

The Simultaneous wavelengths of 870 nm and 930 nm demonstrates little change from the control in the rate of Lipolysis in vitro at the following ranges.

TABLE III

| NIMEL OUTPUT POWER (W) 870 NM + 930 NM | BEAM SPOT 6 CM DIAMETER | TREATMENT TIME (SEC) | TOTAL ENERGY (JOULES) | ENERGY DENSITY (RADIANT EXPOSURE) ($J/cm^2$) | POWER DENSITY (IRRADIANCE) ($W/cm^2$) |
|---|---|---|---|---|---|
| Plate 7 0.4 W + 0.4 W | 28.26 cm2 | 10 min 600 sec | 480 J | 16.7 $J/cm^2$ | 0.027 $W/cm^2$ |

TABLE III-continued

| Plate | Time After Irradiation (min.) | Treated 1 | Control 1 | Control 2 |
|---|---|---|---|---|
| | | Glycerol Concentrations Gly Conc. (micro. M) | | |
| 7 | 30 | 20.0000 | 21.5385 | 17.6923 |
| 7 | 60 | 41.9231 | 45.0000 | 38.4615 |
| | | Free Fatty Acid Concentrations FFA Conc. (micro. M) | | |
| 7 | 30 | 99.0000 | 119.8333 | 104.8333 |
| 7 | 60 | 175.6667 | 207.3333 | 179.8333 |

| Relative Glycerol Concentrations (Percent of control) | | | Relative Free Fatty Acid Concentrations (Percent of control) | | |
|---|---|---|---|---|---|
| Plate | Time After Irradiation (Min.) | T1 % Cont | Plate | Time After Irradiation (Min.) | T1 % Cont |
| 7 | 30 | 113.04 | 7 | 30 | 94.44 |
| 7 | 60 | 109.00 | 7 | 60 | 97.68 |

The Control single wavelength of 810 nm demonstrates little effect to slight suppression of Lipolysis in vitro at the following ranges.

TABLE IV

| NIMEL OUTPUT POWER (W) 810 NM | BEAM SPOT 6 CM DIAMETER | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) |
|---|---|---|---|---|---|
| Plate 3 0.5 W | 28.26 cm$^2$ | 20 min 1200 sec | 600 J | 20.4 J/cm$^2$ | 0.017 W/cm$^2$ |

| | Glycerol Concentrations | | | Free Fatty Acid Concentrations | | |
|---|---|---|---|---|---|---|
| Plate, time after irradiation | Parameters | Gly Conc (micro M) T1 | Gly Conc (micro M) C1 | Plate, time after irradiation | Parameters | FFA Conc (micro M) T1 | FFA Conc (micro M) C1 |
| 6, 15 min | 810 nm, 0.5 W, 1200 sec, | 14.6154 | 12.3077 | 6, 15 min | 810 nm, 0.5 W, 1200 sec, | 18.1667 | 31.5000 |
| 6, 75 min | 810 nm, 0.5 W, 1200 sec, | 26.1538 | 29.6154 | 6, 75 min | 810 nm, 0.5 W, 1200 sec, | 89.0000 | 119.0000 |

Dosimetry Values for Optical Augmentation of Leptin Secretion

The single wavelength of about 930 nm demonstrates approximately 43% Augmentation of Leptin Secretion in vitro at the following range during augmented lipolysis.

TABLE V

| NIMEL OUTPUT POWER (W) 930 NM | BEAM SPOT 6 CM DIAMETER | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) |
|---|---|---|---|---|---|
| Plate 3 0.5 W | 28.26 cm2 | 20 min 1200 sec | 600 J | 20.4 J/cm$^2$ | 0.017 W/cm$^2$ |

TABLE V-continued

| | Leptin Concentrations (pg/mL) - Calculations | | | | |
|---|---|---|---|---|---|
| Plate | Parameters | T Ave | C Ave | NC Ave | % of Control |
| 1 | 930 nm, 0.5 W, 600 sec, 6 cm Dia | 23.6111 | 30.0000 | 33.3333 | 78.7% |
| 2 | 930 nm, 0.5 W, 900 sec, 6 cm Dia | 41.3889 | 41.1111 | 21.9444 | 100.7% |
| 3 | 930 nm, 0.5 W, 1200 sec, 6 cm Dia | 17.5000 | 12.2222 | 20.5556 | 143.2% |
| 5 | 870 nm, 0.5 W, 1200 sec, 6 cm Dia | 25.2778 | 28.0556 | 31.1111 | 90.1% |
| 6 | 810 nm, 0.5 W, 1200 sec, 6 cm Dia | 44.4444 | 36.1111 | 33.6111 | 123.1% |

Dosimetry Values for Optical Augmentation of Leptin Secretion

The single wavelength of about 810 nm demonstrates approximately 23% Augmentation of Leptin Secretion in vitro at the following range during normal lipolysis as shown in Table V above.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of reducing lipid level in an adipocyte, without generating significant heat in, or significant damage to the adipocyte, comprising the steps of:
    irradiating a target site on an individual's skin above adipose tissue with optical radiation having wavelengths in the range of 925 nm to 935 nm at a dosimetry from 0.015 W/cm^2 to 1.0 W/cm^2; and
    directing the optical radiation to the target site with a top hat distribution having a spot size with an area of at least 1.13 cm^2.

2. The method according to claim 1, further comprising initiating at least one adipocyte biochemical processes with exercise immediately before or simultaneous with the irradiation.

3. The method according to claim 1, wherein at least one of the biochemical processes of adipocytes is selected from lipolysis, and leptin production.

4. The method according to claim 1, further comprising initiating at least one biochemical processes with exercise simultaneous with the irradiation.

5. The method according to claim 1, wherein the optical radiation is provided for a time of from 10 to 120 minutes.

6. The method according to claim 1, wherein the optical radiation is provided for a time of from 15 to 100 minutes.

7. The method according to claim 1, wherein the optical radiation is provided for a time of from 20 to 80 minutes.

8. The method according to claim 1, wherein the dosimetry provides an energy density from 10 J/cm^2 to 10,000 J/^2 at the skin surface above the adipose tissue.

9. The method according to claim 1, wherein the dosimetry provides an energy density from 50 J/cm^2 to 8,000 J/^2 at the skin surface above the adipose tissue.

10. The method according to claim 1, wherein the dosimetry provides an energy density from 100 J/cm^2 to 5,000 J/^2 at the skin surface above the adipose tissue.

11. The method according to claim 1, further comprising delivering the optical radiation to the target site by one or more LEDs or LED arrays with aspheric collimating lenses within an article of clothing or a wrap.

12. The method according to claim 1, comprising causing biochemical processes within the adipocytes that are normally antagonistic to each other to function synergistically.

13. A device for reducing fat comprising:
    at least one light source configured to irradiate a target site on an individual's skin above adipose tissue with optical radiation having wavelengths in the range of 925 nm to 935 nm at a dosimetry from 0.015 W/cm^2 to 1.0 W/cm^2 to modulate at least one of the innate biochemical processes of adipocytes; and
    an optical delivery device configured to direct the optical radiation to the target site with a top hat distribution having a spot size with an area of at least 1.13 cm^2;
    wherein said at least one light source is attached to an item of clothing.

14. The device according to claim 13, wherein it is incorporated into a piece of an exercise equipment or other apparatus as an accessory item.

15. The device according to claim 13, the optical radiation has a wavelength from 925 nm to 935 nm.

16. The device according to claim 13, further comprising a controller adapted to control said optical radiation to provide a succession of radiation pulses.

17. The device according to claim 16, wherein the controller is further adapted to control the intensity of said radiation pulses.

18. The device according to claim 16, wherein the controller is adapted to control the repetition rate of said radiation pulses.

19. The method according to claim 1, comprising modulating at least one of the innate biochemical processes to stimulate leptin production.

20. The method according to claim 2, comprising accelerating exercise initiated biochemical lipolysis through optically mediated mechano-transduction.

21. The method according to claim 1, comprising accelerating pharmacologically initiated biochemical lipolysis through optically mediated mechano-transduction.

22. A method comprising:
    increasing leptin production in an adipocyte without generating significant heat in, or significant damage to the adipocyte, the step of increasing leptin comprising:
    irradiating a target site on an individual's skin above adipose tissue with optical radiation having wavelengths in the range of 925 nm to 935 nm at a dosimetry from 0.015 W/cm^2 to 1.0 W/cm^2; and
    directing the optical radiation to the target site with a top hat distribution having a spot size with an area of at least 1.13 cm^2.

* * * * *